United States Patent [19]

Hasegawa et al.

[11] Patent Number: 4,918,170
[45] Date of Patent: Apr. 17, 1990

[54] PROCESS FOR PRODUCING GANGLIOSIDES

[75] Inventors: Akira Hasegawa; Makoto Kiso, both of Gifu, Japan

[73] Assignee: Wako Pure Chemical Industries, Ltd., Osaka, Japan

[21] Appl. No.: 352,595

[22] Filed: May 16, 1989

[30] Foreign Application Priority Data

Aug. 12, 1988 [JP] Japan .................................. 63-201108

[51] Int. Cl.$^4$ ........................ C07H 1/00; C07G 37/00; C07G 17/00; A01N 43/04
[52] U.S. Cl. ........................................ 536/1.1; 536/53; 536/55.1; 536/55.3; 536/124; 514/54
[58] Field of Search ................. 536/1.1, 53, 55.1, 55.2, 536/55.3, 124, 121, 122; 514/54

[56] References Cited

FOREIGN PATENT DOCUMENTS 166442 1/1986 European Pat. Off. .............. 536/53

OTHER PUBLICATIONS

Glyconjugate J. (1985), 2:5-9; Sugimoto, Mamoru and Ogawa, Tomoya; *Synthesis of a Hematoside ($G_{M3}$-Ganglioside) and a Stereoisomer*.
Carbohydrate Research, 163 (1987), 209-225, Numata, Masaaki; Sugimoto, Mamory; Kioke, Katsuya and Ogawa, Tomoya, *Total Synthesis of Sialosylcerebroside, $GM_4$*.

Primary Examiner—Ronald W. Griffin
Assistant Examiner—Everett White
Attorney, Agent, or Firm—Armstrong, Nikaido, Marmelstein, Kubovcik & Murray

[57] ABSTRACT

The present invention provides a novel process for producing gangliosides such as $GM_3$ and $GM_4$ and analogues thereof. This process has the excellent characteristics in that in introduction of ceramide into sialooligosaccharides, first an azidosphingosine derivative is introduced and then the azido portion is reduced to effect N-acylation. The present invention has a conspicuous effect in that the yield is markedly improved as compared with conventional processes.

4 Claims, No Drawings

PROCESS FOR PRODUCING GANGLIOSIDES

BACKGROUND OF THE INVENTION

The present invention relates to a novel process for producing various gangliosides and analogues thereof which are expected to be used as medicines for curing dementia and anticancer medicines.

Ganglioside is a general term for sphingolipids having sialic acid and are given abbreviations such as GM1, GM2, GM3, GM4, GD2, GD3, GT2, GT3, and GT1b depending on their structures, especially sugar chain structures and they are widely present in living tissues of higher animals. Recently, gangliosides have been noted since it has been clarified that gangliosides have activity of an enhancement factor of proliferation and differentiation as acceptor molecules of hormones and bacterial toxin.

However, there have been very few examples of chemical synthesis of gangliosides and only a few reports have been made on synthesis of gangliosides, namely, synthesis of GM3 in Glycoconjugate J., 2, 5–9 (1985), synthesis of GM4 in Carbohydr. Res., 163, 209–225 (1987), etc. These known processes for preparation of gangliosides are very low in yield and are far from being put into practical use. Thus, development of a process for producing gangliosides and analogues thereof more effectively and in high yield has been desired.

SUMMARY OF THE INVENTION

The object of the present invention is to provide a process for producing gangliosides and analogues thereof such as $GM_3$, $GM_4$ and the like in more effectively and high yields and further to provide useful intermediates therefor.

DESCRIPTION OF THE INVENTION

The present invention comprises the following construction for attaining the above object.

(1) A process for producing a ganglioside represented by the following formula [V], [VI] or [VII]:

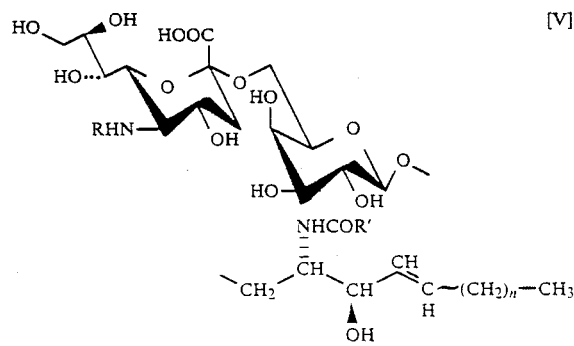

(wherein R represents an aliphatic acyl group, R' represents a saturated or unsaturated straight chain or branched chain alkyl group of 1–30 carbon atoms and n represents an integer of 0–20),

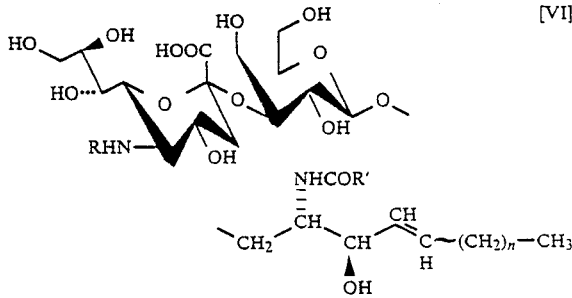

(wherein R, R' and n are as defined above),

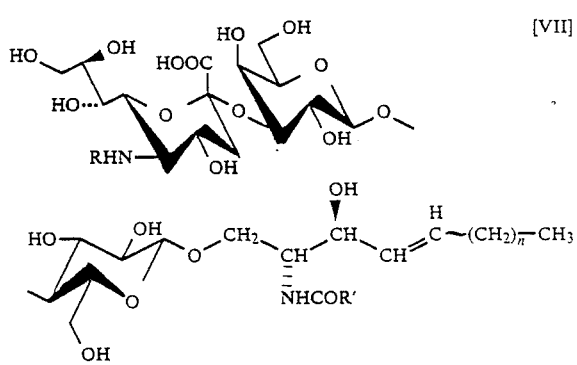

(wherein R, R' and n are as defined above) which comprises eliminating the protecting group for hydroxyl group at 1-position of the reducing-end-glucose residue of 2-α-O-glycoside compound of sialic acid represented by the following formula [I], [II] or [III]:

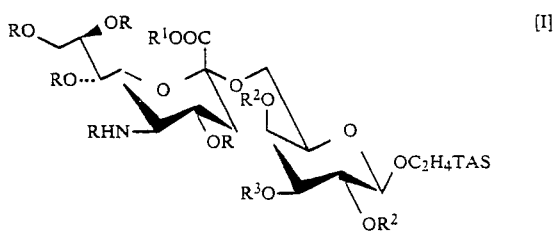

(wherein $R^1$ represents a lower alkyl group, $R^2$ and $R^3$ each represents an acyl group and TAS denotes trialkylsilyl group, R is as defined above),

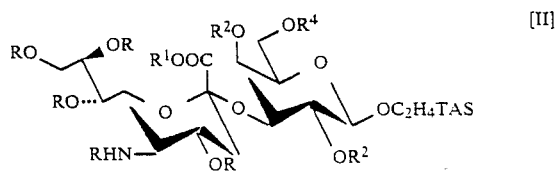

(wherein $R^2$ and $R^4$ each represents an acyl group and R, $R^1$ and TAS are as defined above),

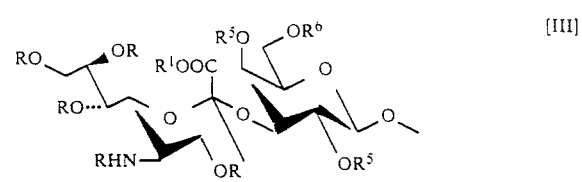

(2) A compound represented by the following formula [VIII], [IX] or [X]:

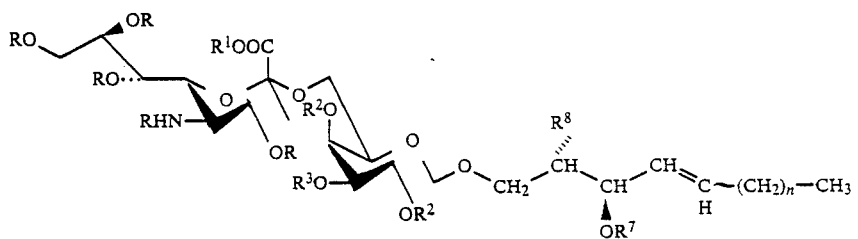
[VIII]

[wherein $R^8$ represents $-N_3$, $-NH_2$ or $-NHCOR'$ ($R'$ is as defined above) and R, $R^1$, $R^2$, $R^3$, $R^7$ and n are as defined hereabove],

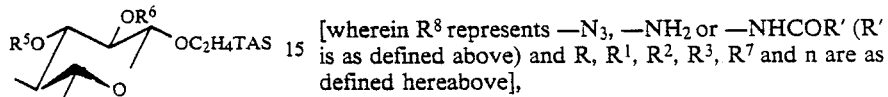

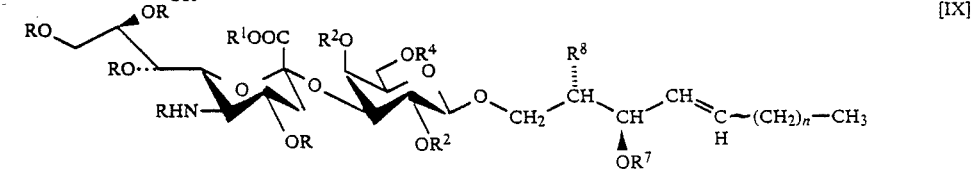
[IX]

(wherein R, $R^1$, $R^2$, $R^4$, $R^7$, $R^8$ and n are as defined hereabove),

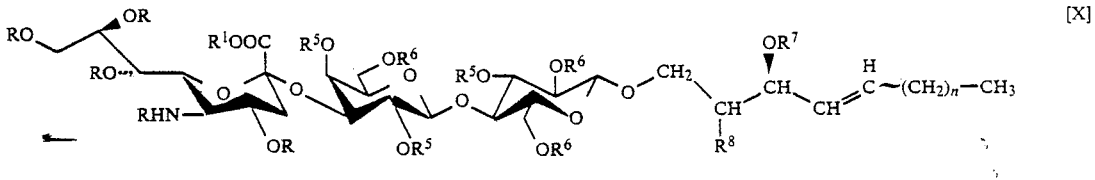
[X]

(wherein R, $R^1$, $R^5$, $R^6$, $R^7$, $R^8$ and n are as defined hereabove).

R in the formulas [I], [II], [III], [V], [VI], [VII], [VIII], [IX] and [X] includes aliphatic acyl groups such as acetyl group, propionyl group and butanoyl group. $R^1$ in the formulas [I], [II], [III], [V], [VI], [VII], [VIII], [IX] and [X] includes lower alkyl groups such as methyl group, ethyl group, propyl group and butyl group. $R^2$ and $R^3$ in the formulas [I] and [VIII], $R^2$ and $R^4$ in the formulas [II] and [IX] and $R^5$ and $R^6$ in the formulas [III] and [X] independently represent acyl groups such as acetyl group, propionyl group, butanoyl group and benzoyl group. TAS in the formulas [I], [II] and [III] denotes trialkylsilyl groups such as trimethylsilyl group, triethylsilyl group, triisopropylsilyl group, and dimethyl t-butylsilyl group. $R^7$ in the formulas [IV], [VIII], [IX] and [X] includes acyl groups such as benzoyl group, acetyl group, propionyl group, and butanoyl group. n in the formulas [IV]–[X] denotes an integer of 0–20. $R'$ in the formulas [V], [VI] and [VII] includes saturated or unsaturated alkyl groups of 1–30 carbon atoms such as $-CH_3$, $-C_2H_5$, $-C_3H_7$, $-C_4H_9$, $-C_5H_{11}$, $-C_7H_{15}$, $-C_9H_{19}$, $-C_{11}H_{23}$, $-C_{13}H_{27}$, $-C_{15}H_{31}$, $-C_{17}H_{35}$, $-C_{23}H_{47}$, $-C_{30}H_{61}$, $-C_{17}H_{31}$, $-C_{17}H_{32}$, and $-C_{17}H_{33}$. $R^8$ in the formulas [VIII], [IX] and [X] represents $-N_3$, $-NH_2$ or $-NHCOR'$ wherein $R'$ includes saturated or unsaturated alkyl groups of 1-30 carbons as exemplified above.

The process for producing a ganglioside according to the present invention is generally practised in the following manner.

-continued (wherein $R^5$ and $R^6$ each represents an acyl group and R, $R^1$ and TAS are as defined above), reacting the thus treated compound with trichloroacetonitrile in the presence of a basic catalyst to convert the hydroxyl group at 1-position of the reducing-end-glucose residue to trichloroacetoimide $-OC(NH)CCl_3$, reacting the product with an azidosphingosine derivative represented by the formula [IV]:

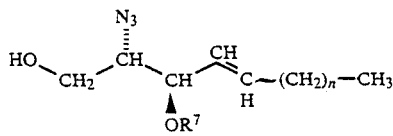

(wherein $R^7$ represents an acyl group and n is as defined above) to replace the $-OC(NH)CCl_3$ group at 1-position of the reducing-end-glucose residue with the following group:

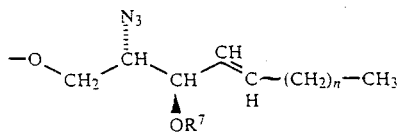

(wherein $R^7$ and n are as defined above), then reducing the product, N-acylating the reduction product with a fatty acid and thereafter successively deprotecting the protecting group for hydroxyl group and protecting group for carboxyl group.

That is, first, a 2-α-O-glycoside compound of sialic acid represented by the formula [I], [II] or [III] is treated with a fluorine compound capable of generating fluoride ion (F−), such as BF$_3$-ether, NaBF$_4$, KBF$_4$, or LiBF$_4$ or a Lewis acid such as FeCl$_3$, if necessary, in a suitable non-polar solvent, thereby to eliminate the protecting group for hydroxyl group at 1-position on reduced terminal, namely, trialkylsilylethyl group. Normally, the reaction is carried out at a low temperature (about 0° C.~room temperature) and reaction time is about 1~10 hours. After termination of the reaction, the reaction mixture may be subjected to conventional after-treatments such as extraction with solvent and distilling off of the solvent. If necessary, the product may be purified by column chromatography and the like. Thereafter, the resulting compound is reacted with trichloroacetonitrile in the presence of a basic catalyst in a non-polar solvent such as dichloromethane, dichloroethane or chloroform to convert the hydroxyl group at 1-position of the reducing-end-glucose residue to trichloroacetoimide —OC(NH)CCl$_3$. Examples of the basic catalyst are organic bases such as 1,5-diazabicyclo[5.3.0]undec-5-ene (DBU) and 1,5-diazabicyclo[4.3.0]non-5-ene (DBN) and inorganic bases such as NaH, K$_2$CO$_3$ and Na$_2$CO$_3$. Generally, the reaction is carried out at a low temperature, for example, about 0° C. or lower and reaction time is several hours which is sufficient. After termination of the reaction, the reaction mixture may be subjected to conventional after-treatments such as distilling off of solvent and, if necessary, may be purified by column chromatography or the like.

The resulting 2-α-O-glycoside compound of sialic acid having —OC(NH)CCl$_3$ group at 1-position of the reducing-end-glucose residue is reacted with an azidosphingosine derivative represented by the above formula [IV] in a non-polar solvent such as dichloromethane or dichloroethane in the presence of a Lewis acid such as BF$_3$-ether or methyl triflate (methyl trifluoromethanesulfonate), whereby a compound where the above-mentioned —OC(NH)CCl$_3$ group is substituted by the group represented by the formula:

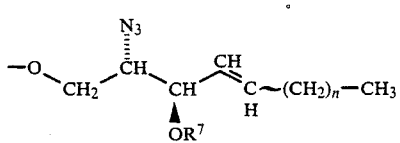

(wherein R$^7$ and n are as defined hereabove), namely, the novel compound of the present invention represented by the formula [VIII], [IX] or [X] where R$^8$=—N$_3$ can be obtained in a high yield. The reaction is normally carried out in the presence of a dehydrating agent such as a molecular sieves. The reaction temperature is usually about 0° C. and the reaction time is usually about 1-10 hours. After termination of the reaction, the reaction mixture may be subjected to conventional after-treatments such as filtration to remove insoluble matters, extraction with solvent and distilling off of solvent and, if necessary, may be purified by column chromatography or the like. When the resulting compound is reduced under a weak reducing condition, the compound of the present invention represented by the formula [VIII], [IX] or [X] where R$^8$=—NH$_2$ can be obtained in a high yield. When this compound is further N-acylated with a fatty acid, the novel compound of the present invention represented by the formula [VIII], [IX] or [X] where R$^8$=—NHCOR' (R' is as defined hereabove) can be obtained in a high yield. The reducing agent used for reducing the azido compound as mentioned-above is preferably an acidic reducing agent such as hydrogen sulfide, but should not be limited thereto and can be any reducing agent which has reducibility of azido and does not reduce double bonds and does not eliminate acyl protecting groups. Reaction conditions naturally vary depending on the reducing agent used and reducing method and can be optionally chosen. For example, in the case of using hydrogen sulfide as a reducing agent, reaction is usually carried out in pyridine-water mixed solvent (e.g., a mixed solvent comprising pyridine:2-10 vol. and water:1 vol.) at about room temperature for 10-60 hours. After termination of the reaction, after-treatments may be effected in conventional manner. Normally, the reaction mixture is concentrated to dryness and then is directly subjected to the subsequent step, namely, N-acylation without isolation of amino compound. The fatty acid used for the N-acylation includes saturated or unsaturated fatty acids of 2-31 carbon atoms which may be either straight chain or branched chain acids. As examples thereof, mention may be made of acetic acid, propionic acid, butyric acid, capric acid, lauric acid, myristic acid, palmitic acid, octadecanoic acid (stearic acid), tetracosanoic acid (lignoceric acid), melissic acid, oleic acid, and linolic acid, but it is needless to say that they are not limited to these acids. The reaction of N-acylation is usually carried out in a suitable reaction solvent such as dichloromethane, dichloroethane or chloroform in the presence of a dehydration condensing agent such as 1,3-dicyclohexylcarbodiimide (DCC) or 1-ethyl-3-(3'-dimethylaminopropyl)carbodiimide (WSC) at room temperature or somewhat higher temperature for from several hours to several days. After the reaction, the reaction mixture may be subjected to conventional after-treatments such as extraction with solvent and distilling off of solvent and, if necessary, may further be purified by column chromatography or the like.

The protecting groups for hydroxyl group and carboxyl group of the resulting compound of the formula [VIII], [IX] or [X] where R$^8$=—NHCOR' are successively eliminated by conventional methods to obtain the objective ganglioside represented by the formula [V], [VI] or [VII] in a high yield. Elimination of protecting group (acyl group) for hydroxyl group can be performed by dissolving the compound obtained by the N-acylation in an alcohol solvent such as methanol or ethanol (preferably fully dehydrated one), adding thereto a suitable amount of an alkali, for example, a metal alcoholate such as sodium methylate or sodium ethylate and carrying out the reaction at 0°-50° C. for several to several ten hours with stirring. Elimination of protecting groups for carboxyl group can be performed by adding a small amount of water to the reaction mixture obtained after the elimination of the acyl protecting group and carrying out further reaction for several to several ten hours with stirring. After completion of the hydrolysis reaction, the reaction mixture may be subjected to conventional after-treatments such as neutralization, for example, by a cation exchange resin, filtration, and concentration to dryness of the filtrate.

The 2-α-O-glycoside compound of sialic acid used in the process of the resent invention and represented by the formulas [I], [II] and [III] can be easily synthesized, for example, in the following manner.

That is, first, an alkylthiosialic acid derivative represented by the following formula [*I] and disclosed in Japanese Patent Kokai No. 63-41494 as a sugar donor for formation of glycoside:

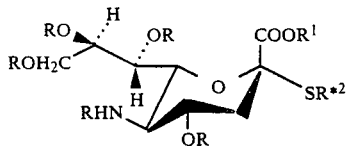

(wherein $R^{*2}$ represents a lower alkyl group and R and $R^1$ are as defined above) is reacted with a compound represented by the formula [*II], [*III] or [*IV] which is a sugar acceptor:

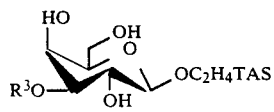

(wherein $R^3$ and TAS are as defined above),

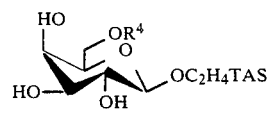

(wherein $R^4$ and TAS are as defined above),

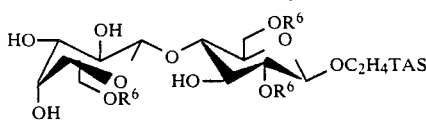

(wherein $R^6$ and TAS are as defined above) in a polar solvent having no hydroxyl group such as acetonitrile, propionitrile, butyronitrile or nitromethane (preferably fully dried one) in the presence of a Lewis acid such as methyl triflate (methyl trifluoromethanesulfonate), trimethylsilyl triflate (trimethylsilyl trifluoromethanesulfonate) or dimethyl(methylthio)sulfonium triflate (DMTST) at a low temperature, for example, room temperature or less, preferably lower than −5° C. for several hours to several ten hours. After the reaction, reaction mixture may be subjected to conventional after-treatments such as removal of insoluble matters by filtration and concentration of filtrate and, if necessary, may be purified by column chromatography or the like.

The resulting 2-α-O-glycoside compound of sialic acid is acylated by conventional methods, for example, by reacting it with acetic anhydride in anhydrous pyridine at room temperature for several hours to several ten hours, whereby 2-α-O-glycoside compounds of sialic acid represented by the formula [I], [II] and [III] used in the present invention can be easily obtained.

The compound represented by the formula [*II] used as a sugar acceptor for forming glycoside can be easily obtained, for example, by reacting a compound represented by the formula [*IIa]:

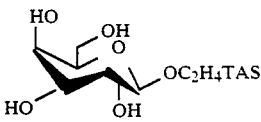

(wherein TAS is as defined above) with an acylating agent (e.g., benzoyl chloride and acetic anhydride) in accordance with ordinary acylation method, in the presence of a base such as pyridine or triethylamine, if necessary, under cooling or by reacting a compound represented by the formula [*IIa] with di-n-butyltin oxide, tetra-n-butylammonium bromide and benzyl bromide in a non-polar solvent such as benzene, toluene, chloroform, dichloromethane or dichloroethane for 1-10 hours under heating in accordance with ordinary methods of benzylation of hydroxyl groups. Compounds obtained by the former method are compounds of the formula [*II] in which $R^3$ is an acyl group such as benzoyl group or acetyl group and compounds obtained by the latter method are compounds of the formula [*II] in which $R^3$ is benzyl group.

The compound represented by the formula [*III] used as a sugar acceptor can be easily obtained, for example, in the following manner.

That is, first, a compound represented by the formula [*II] where $R^3$ is benzyl group is prepared by the latter method mentioned above using a compound represented by the formula [*IIa] as a starting material. Then, the resulting compound is reacted with an acylating agent (e.g., benzoyl chloride and acetic anhydride) in accordance with ordinary acylation methods in the presence of a base such as pyridine or triethylamine, if necessary, under cooling to selectively acylate the hydroxyl group at 6-position to obtain a compound represented by the formula [*IIIa]:

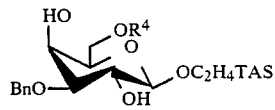

(wherein Bn represents a benzyl group and $R^4$ and TAS are as defined above). Then, this compound is reduced in accordance with conventional methods using, for example, formic acid as a hydrogen donor and palladium-carbon as a catalyst to obtain the compound of the formula [*III] with the modification group at 6-position being maintained and with only the benzyl group at 3-position being eliminated.

The compound represented by the formula [*IV] can be easily prepared, for example, by the following method.

That is, first, a compound represented by the formula [*IVa]:

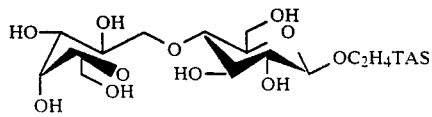

(wherein TAS is as defined above) is reacted with di-n-butyltin oxide, tetra-n-butylammonium bromide and benzyl bromide in a non-polar solvent such as benzene, toluene, chloroform, dichloromethane or dichloroethane for 1-10 hours under heating in accordance with ordinary methods of benzylation of hydroxyl group to obtain a compound represented by the formula [*IVb]:

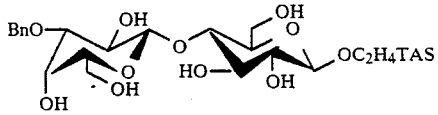

[*IVb]

(wherein TAS and Bn are as defined above). Then, in accordance with ordinary acylation method, this compound is reacted with an acylating agent (e.g., benzoyl chloride and acetic anhydride) in the presence of a base such as pyridine or triethylamine, if necessary, under cooling to selectively acylate the hydroxyl groups at 2-position, 6-position and 6'-position to obtain a compound represented by the formula [*IVc]:

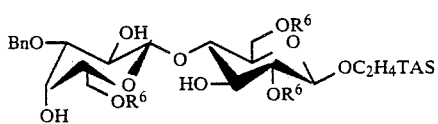

[*IVc]

(wherein $R^6$, Bn and TAS are as defined above). Then, in accordance with conventional method, this compound is reduced using, for example, palladium-carbon as a catalyst and formic acid as a donor for hydrogen to obtain a compound represented by the formula [*IV] with elimination of only the benzyl group at 3'-position.

The compound represented by the formula [*IIa] which is a starting material for preparation of the compounds represented by the formulas [*II] and [*III] and the compound represented by the formula [*IVa] which is a starting material for preparing the compound represented by the formula [*IV] both can be easily obtained by the following method using the corresponding sugars or amino sugars which was found by the inventors (Japanese Patent Application No. 63-1707).

First, the corresponding sugar or amino sugar is acylated by conventional method using an acylating agent (e.g., acetic anhydride and acetyl chloride) and then a halogen group is introduced at 1-position using hydrogen bromide or the like by conventional method, followed by reacting with TASC$_2$H$_4$OH (wherein TAS is as defined above) in the presence of a condensing agent such as Hg(CN)$_2$ and HgBr$_2$, Ag$_2$CO$_3$ and AgClO$_4$, Ag$_2$CO$_3$ and I$_2$, AgClO$_4$ or Hg(CN)$_2$ to obtain the sugar derivative or an amino sugar derivative where the hydroxyl group at 1-position is protected with 2-(trialkylsilyl)ethyl group and the other hydroxyl groups are protected with the acyl group. The compound represented by the formula [*IIa] or [*IVa] can be easily obtained by subjecting the resulting sugar derivative or amino sugar derivative to elimination of the protecting acyl group by conventional methods, for example, treatment with sodium methylate in methanol.

The alkylthiosialic acid derivative represented by the formula [*I] used as a sugar donor for formation of glycoside can be easily prepared through the following route, for example, in accordance with the method disclosed in Japanese Patent Kokai No. 63-41494 and the thus obtained alkylthiosilalic acid derivative may be used.

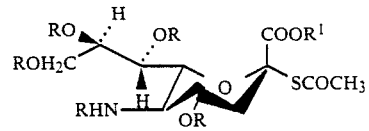

(wherein R and $R^1$ are as defined above).

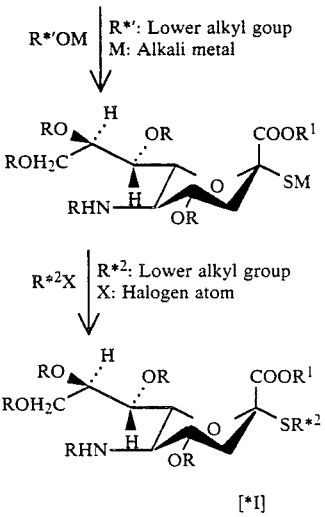

[*I]

DMTST used in the reaction for formation of glycoside is prepared as required from dimethyl disulfide and methyl trifluoromethanesulfonate in accordance with the method disclosed in J. Chem. Soc., Perkin Trans. II, 1569–1572 (1982).

The azidosphingosine derivative represented by the formula [IV] and used in the process of the present invention can be easily obtained by synthesizing an azidosphingosine represented by the formula [IVa]:

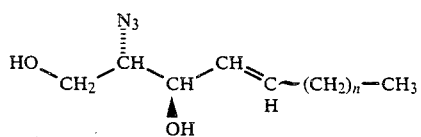

[IVa]

in accordance with the method disclosed in Japanese Patent Kokai No. 62-207247, protecting the primary hydroxyl group at 1-position thereof with a suitable protecting group such as dimethyl t-butylsilyl group, then acylating the hydroxyl group at 3-position with an acylating agent such as benzoyl chloride or acetic anhydride in accordance with conventional method and thereafter eliminating the hydroxyl group at 1-position, for example, with BF$_3$-ether.

The following nonlimiting examples illustrate the present invention.

The abbreviations used in the explanation of NMR have the following meanings.

Me: methyl group; Ac: acetyl group;

Bz: benzoyl group

REFERENCE EXAMPLE 1

Preparation of 1-[2-(trimethylsilyl)ethyl]-2,3,4,6-tetra-O-acetyl-β-D-galactopyranoside 5.04 g of 1,2,3,4,6-penta-O-acetyl-D-galactopyranoside was dissolved in 50 ml of sufficiently dehydrated dichloromethane and thereto was added 25 g of 30% acetic acid solution of hydrogen bromide at 0° C., followed by reaction with stirring at room temperature for 1.5 hour. After termination of the reaction, the reaction mixture was concentrated under reduced pressure to obtain a syrupy product. This was dissolved in 25 ml of dichloromethane and thereto was added 5 g of Molecular Sieves 4Å and reaction was allowed to proceed for 5 hours with stirring (Reaction mixture-1). Separately, 7 g of $Ag_2CO_3$, 2.7 g of $AgClO_4$, 3.66 ml of trimethylsilyl ethanol and 5 g of Molecular Sieves 4Å were suspended in 25 ml of sufficiently dehydrated dichloromethane and reaction was allowed to proceed for 5 hours with stirring (Reaction mixture-2). Then, reaction mixture-1 and reaction mixture-2 were mixed and reaction was allowed to proceed overnight with stirring. After the termination of the reaction, the reaction mixture was filtered through Celite and the filtrate was concentrated under reduced pressure to obtain a syrupy product. This was purified by column chromatography [packing material: Wakogel C-200 (trademark for packing material supplied by Wako Pure Chemical Industries, Ltd.), eluent: $CH_2Cl_2$] to obtain 4.2 g of syrup of 1-[2-(trimethylsilyl)ethyl]-2,3,4,6-tetra-O-acetyl-β-D-galactopyranoside. Yield: 72.5%.

Elementary analysis:

| | | |
|---|---|---|
| Calcd. (%): | C: 50.88, | H: 7.29 |
| Found (%): | C: 50.95, | H: 7.30 |

$[\alpha]_D = -9.49°$ (C = 1.01, $CHCl_3$)

REFERENCE EXAMPLE 2

Preparation of 1-[2-(trimethylsilyl)ethyl]-β-D-galactopyranoside [hereinafter referred to as Compound (1)]

3.36 g of 1-[2-(trimethylsilyl)ethyl]-2,3,4,6-tetra-O-acetyl-β-D-galactopyranoside obtained in Reference Example 1 was dissolved in 30 ml of sufficiently dehydrated methanol and thereto was added a catalytic amount of sodium methylate, followed by stirring for 1 hour. After termination of the reaction, the reaction mixture was neutralized with Amberlite IR-120 (trademark for H+ type ion exchange resin supplied by Organo Co.) and the product was subjected to filtration. The filtrate was concentrated under reduced pressure to quantitatively obtain a crystal of Compound (1).

Elementary analysis:

| | | |
|---|---|---|
| Calcd. (%): | C: 47.12, | H: 8.63 |
| Found (%): | C: 47.35, | H: 8.71 |

$[\alpha]_D = -22.06°$ (C = 1.012, $CH_3OH$)

REFERENCE EXAMPLE 3

Preparation of 2-(trimethylsilyl)ethyl 3-O-benzoyl-β-D-galactopyranoside [hereinafter referred to as Compound (2)]

1.0 g of Compound (1) was dissolved in 10 ml of pyridine and cooled to −50° C. Thereto was added dropwise a solution prepared by dissolving 603 mg of benzoyl chloride in 10 ml of dichloromethane which was cooled to −50° C., over a period of 10 minutes. Reaction was allowed to proceed for 3 hours with stirring, methanol was added and this was concentrated. The residue was extracted with addition of dichloromethane. The dichloromethane layer was washed with water, dried over anhydrous $Na_2SO_4$ and concentrated. The resulting syrup was purified by a column chromatography [packing material: Wakogel C-200, eluent: $CH_2Cl_2/CH_3OH=40/1$] to obtain 920 mg of Compound (2). Yield: 67%.

$[\alpha]_D = +30.50°$ (C=1.20, $CHCl_3$)

IR $\nu_{max}^{film}$ (cm$^{-1}$);
3700–3100 (OH), 3000–2700 (CH), 1710 (ester), 860, 840 (trimethylsilylethyl), 710 (phenyl).

NMR ($CDCl_3$—$CD_3OD$) δppm: 8.08–7.38 (m, 5H, —OBz), 5.04 (dd, 1H, $J_{2,3}$=10.26 Hz, $J_{3,4}$=3.21 Hz, H-3), 4.39 (d, 1H, $J_{1,2}$=7.70 Hz, H-1), 4.25 (broad d, 1H, H-4), 4.01 (dd, 1H, H-2), 4.02 (m, 1H, —OC$\underline{H}^2$CH$_2$Si), 3.61 (m, 1H, —OC$\underline{H}^1$CH$_2$Si), 1.00 (m, 2H, —OCH$_2$C$\underline{H}_2$Si), 0 (s, 9H, Me$_3$S$\underline{i}$).

REFERENCE EXAMPLE 4

Preparation of 2-(trimethylsilyl)ethyl 3-O-benzyl-β-D-galactopyranoside [hereinafter referred to as Compound (3)]

1.90 g of Compound (1) was suspended in 50 ml of benzene and to the suspension was added 2.54 g of (n-$C_4H_9$)$_2$SnO, followed by stirring at 80° C. for 5 hours. Thereto were added 1.10 g of (n-$C_4H_9$)$_4$NBr and 12 ml of benzyl bromide and reaction was allowed to proceed for further 3 hours with stirring. After the reaction, the reaction mixture was concentrated under reduced pressure. n-Hexane was added to the residue and excess benzyl bromide was removed by decantation. The resulting syrup was subjected to column chromatography [packing material: Wakogel C-200, eluent: $CH_2Cl_2/CH_3OH=125/1$] to obtain 1.93 g of Compound (3). Yield: 76.6%.

$[\alpha]_D = +5.6°$ (C=0.50, $CH_2Cl_2$)

IR $\nu_{max}^{film}$ (cm$^{-1}$);
3700–3100 (OH), 3000–2700 (CH), 860, 840 (trimethylsilylethyl), 750, 700 (phenyl).

NMR ($CDCl_3$—$CD_3OD$) δppm: 7.26–7.38 (m, 5H, —CH$_2$C$_6$H$_5$), 4.67–4.77 (2d, 2H, —C$\underline{H}_2$—C$_6$H$_5$), 4.24 (d, 1H, $J_{1,2}$=7.7 Hz, H-1), 4.02 (near m, 1H, $J_{3,4}$=3.3 Hz, H-4), 3.80 (m, 2H, H-6), 3.70 (dd, 1H, $J_{2,3}$=9.53 Hz, H-2), 3.60, 4.01 (2m, 2H, —OC$\underline{H}_2$CH$_2$Si), 3.43 (near t, 1H, H-5), 3.39 (dd, 1H, H-3), 1.00 (m, 2H, —CH$_2$C$\underline{H}_2$Si), 0 (2, 9H, Me$_3$Si).

REFERENCE EXAMPLE 5

Preparation of 2-(trimethylsilyl)ethyl 6-O-benzoyl-β-D-galactopyranoside [hereinafter referred to as Compound (5)]

(1) Preparation of 2-(trimethylsilyl)ethyl 6-O-benzoyl-3-O-benzyl-β-D-galactopyranoside [hereinafter referred to as Compound (4)]

3.5 g of Compound (3) obtained in the same manner as in Reference Example 4 was dissolved in a mixed solvent of pyridine 10 ml-dichloromethane 40 ml and was cooled to −50° C. To the solution was added dropwise a solution prepared by dissolving 1.82 g of benzoyl chloride in 20 ml of dichloromethane and reaction was allowed to proceed for 1 hour with stirring. After completion of the reaction, methanol was added, followed by stirring for further 30 minutes. Then, the reaction mixture was concentrated under reduced pressure. The residue was extracted with addition of dichloromethane and the dichloromethane layer was washed with water, dried over anhydrous $Na_2SO_4$ and concentrated under reduced pressure. The resulting syrup was subjected to column chromatography [packing material: Wakogel C-200, eluent: $CH_2Cl_2/CH_3OH=150/1$] to obtain 3.16 g of Compound (4). Yield: 70.5%.

$[α]_D = −1.55°$ (C=0.900, $CHCl_3$)

IR $ν_{max}^{film}$ (cm$^{-1}$);
3700–3150 (OH), 3150–2700 (CH), 1720, 1250 (ester), 860, 840 (trimethylsilyl), 710 (phenyl)

NMR ($CDCl_3$—$CD_3OD$) δppm: 8.08–7.29 (m, 10H, —$CH_2C_6\underline{H}_5$, OBz), 4.77 (s, 2H, —$C\underline{H}_2C_6H_5$), 4.59 (near d, 2H, H-6,6'), 4.29 (d, 1H, $J_{1,2}=7.88$ Hz, H-1), 4.00 (m, 2H, H-4, —$OCH^1CH_2Si$), 3.78 (m, 2H, H-2, H-5), 3.62 (m, 2H, —$OC\underline{H}^2CH_2Si$), 3.47 (dd, 1H, $J_{2,3}=9.43$ Hz, $J_{3,4}=3.30$ Hz, $\underline{H}$-3), 1.03 (m, 2H, —$OCH_2C\underline{H}_2Si$), 0 (s, 9H, $Me_3Si$).

(2) Preparation of Compound (5):

3.50 g of Compound (4) was dissolved in 150 ml of methanol and thereto were added 6 g of 10% palladium-carbon and 2.5 ml of formic acid and reaction was allowed to proceed for 1 hour at 60° C. After the reaction, the reaction mixture was filtered to remove insoluble matters and the filtrate was concentrated under reduced pressure. The resulting syrup was subjected to column chromatography [packing material: Wakogel C-200, eluent: $CH_2Cl_2/CH_3OH=40/1$] to obtain 1.90 g of Compound (5). Yield: 67%.

$[α]_D = −3.69°$ (C=0.92, $CHCl_3$)

IR $ν_{max}^{film}$ (cm$^{-1}$);
3700–3000 (OH), 3000–2800 (CH), 1720, 1250 (ester), 860, 840 (trimethylsilyl), 700 (phenyl)

NMR ($CDCl_3$—$CD_3OD$) δppm: 8.07–7.43 (m, 5H, OBz), 4.59 (d, 2H, J=6.39 Hz, H-6, H-6'), 4.29 (d, 1H, $J_{1,2}=7.33$ Hz, H-1), 3.84 (near t, 1H, $J_{5,6}=6.60$ Hz, H-5), 1.03 (m, 2H, —$OCH_2C\underline{H}_2Si$), 0 (s, 9H, $Me_3Si$).

REFERENCE EXAMPLE 6

Preparation of 2-(trimethylsilyl)ethyl O-(6-O-benzoyl-β-D-galactopyranosyl)-(1→4)-2,6-di-O-benzoyl-β-D-glucopyranoside [hereinafter referred to as Compound (8)]

(1) Preparation of 2-(trimethylsilyl)ethyl O-(3-O-benzyl-β-D-galactopyranosyl)-(1→4)-β-D-glucopyranoside (hereinafter referred to as Compound (6))

6.59 g of 2-(trimethylsilyl)ethyl β-D-lactoside was dissolved in 100 ml of methanol. To the solution was added 4.92 g of $(n-C_4H_9)_2SnO$ and reaction was allowed to proceed for 3 hours with stirring under reflux with heating. After the reaction, the reaction mixture was concentrated under reduced pressure and sufficiently dried. Then 200 ml of benzene was added to the residue to dissolve it. Thereto were added 4.80 g of $(n-C_4H_9)_4NBr$ and 14.2 ml of benzyl bromide and reaction was allowed to proceed for 3 hours with stirring under reflux with heating. After termination of the reaction, the reaction mixture was concentrated under reduced pressure. n-Hexane was added to the residue and excess benzyl bromide was removed by decantation. The resulting syrup was subjected to column chromatography [packing material: Wakogel C-200, eluent: ethyl acetate/n-hexane=4/1] to obtain 5.96 g of Compound (6). Yield: 75.2%.

m.p. 164°–167° C.
$[α]_D = −0.14°$ (C=1.48, $CH_2Cl_2$)

IR $ν_{max}^{film}$ (cm$^{-1}$);
3700–3100 (OH), 3000–2850 (CH), 860, 840 (trimethylsilyl), 740, 700 (phenyl)

NMR ($CD_3OD$) δppm: 7.41–7.21 (m, 5H, —$CH_2$—$C_6\underline{H}_5$), 4.72, 4.58 (2d, 2H, $J_{gem}=11.9$ Hz, —$C\underline{H}_2$—$C_6H_5$), 4.34 (d, 1H, $J_{1',2'}=8.1$ Hz, H-1'), 4.26 (d, 1H, $J_{1,2}=7.7$ Hz, H-1), 3.97 (near d, 1H, $J_{3',4'}=3.3$ Hz, H-4'), 3.35 (dd, 1H, $J_{2',3'}=9.5$ Hz, H-3'), 3.21 (near t, 1H, $J_{2,3}=8$ Hz, H-2), 0.96 (m, 2H, —$OCH_2C\underline{H}_2Si$), −0.02 (s, 9H, $SiMe_3$)

(2) Preparation of 2-(trimethylsilyl)ethyl O-(6-O-benzoyl-3-O-benzyl-β-D-galactopyranosyl-(1→4)-2,6-di-O-benzoyl-β-D-glucopyranoside (hereinafter referred to as Compound (7))

1.32 g of Compound (6) was dissolved in a mixed solvent of pyridine 8 ml and dichloromethane 20 ml, followed by cooling to −50° C. Thereto was added dropwise a solution prepared by dissolving 1.2 ml of benzoyl chloride in 15 ml of dichloromethane and reaction was allowed to proceed for 30 minutes with stirring. After termination of the reaction, to the reaction mixture was added methanol to decompose excess benzoyl chloride. Thereafter, the reaction mixture was concentrated under reduced pressure. The residue was extracted with addition of dichloromethane and the dichloromethane layer was washed with hydrochloric acid and water, dried over anhydrous $Na_2SO_4$ and then concentrated under reduced pressure. The resulting syrup was subjected to column chromatography [packing material: Wakogel C-200, eluent: $CH_2Cl_2/CH_3OH=200/1$] to obtain 1.40 g of Compound (7). Yield: 67%.

$[α]_D = +14.01°$ (C=0.856, $CHCl_3$)

IR $\nu_{max}^{film}$ (cm$^{-1}$):
3700–3100 (OH), 3100–2800 (CH), 1730, 1260 (ester), 860, 840 (triethylsilyl), 710 (phenyl)

NMR (CDCl$_3$—CD$_3$OD) δppm: 8.18–7.38 (m, 20H, OBzx3, —CH$_2$—C$_6$H$_5$), 5.33 (dd, 1H, J$_{1,2}$=8.06 Hz, J$_{2,3}$=8.15 Hz, H-2), 5.04 (dd, 1H, J$_{gem}$=11.91 Hz, H-6), 4.85 (s, 2H, —CH$_2$—C$_6$H$_5$), 4.73 (d, 1H, J$_{1,2}$=8.06 Hz, H-1), 4.63 (dd, 1H, J$_{gem}$=11.90 Hz, J$_{5,6}$=5.86 Hz, H-6), 4.51 (d, 1H, J$_{1',2'}$=7.88 Hz, H-1'), 3.53 (dd, 1H, J$_{2',3'}$=9.53, J$_{3',4'}$=3.30 Hz, H-3'), 0.96 (m, 2H, —OCH$_2$CH$_2$Si), 0 (s, 9H, Me$_3$Si)

(3) Preparation of Compound (8)

1.40 g of Compound (7) was dissolved in 50 ml of methanol and 1.0 g of 10% palladium-carbon and 1 ml of formic acid were added to the solution and reaction was allowed to proceed for 2 hours at 60° C. with stirring. After the reaction, the reaction mixture was filtered to remove insoluble matters and filtrate was concentrated under reduced pressure. The resulting syrup was subjected to column chromatography [packing material: Wakogel C-200, eluent: CH$_2$Cl$_2$/CH$_3$OH=50/1] to obtain 880 mg of Compound (8). Yield: 70%.

[α]$_D$= +11.03° (C=0.58, CHCl$_3$)

IR $\nu_{max}^{film}$ (cm$^{-1}$):
3700–3100 (OH), 3000–2800 (CH), 1720, 1260 (ester), 860, 840 (trimethylsilyl), 700 (phenyl)

NMR (CDCl$_3$—CD$_3$OD) δppm: 8.17–7.40 (m, 15H, OBzx3), 5.33 (dd, 1H, J$_{1,2}$=8.06 Hz, J$_{2,3}$=9.61 Hz, H-2), 4.99 (dd, 1H, J$_{gem}$=10.26 Hz, H-6), 4.81 (dd, 1H, J$_{gem}$=11.91 Hz, J$_{5,6}$=3.30 Hz, H-6), 4.74 (d, 1H, J$_{1',2'}$=8.06 Hz, H-1), 4.64 (dd, 1H, J$_{gem}$=11.90 Hz, J$_{5,6}$=5.86 Hz, H-6), 4.50 (d, 1H, J$_{1',2'}$=7.88 Hz, H-1')

REFERENCE EXAMPLE 7

Preparation of 2-(trimethylsilyl)ethyl O-[methyl(5-acetamido-4,7,8,9-tetra-O-acetyl-3,5-dideoxy-D-glycero-α-D-galacto-2-nonulopyranosyl)onate]-2→6)-3-O-benzoyl-β-D-galactopyranoside [hereinafter referred to as Compound (9)]

0.16 g of Compound (2) obtained in Reference Example 3 and 0.43 g of methyl(methyl 5-acetamido-4,7,8,9-tetra-O-acetyl-3,5-dideoxy-2-thio-D-glycero-α-D-galacto-2-nonulopyranosid)onate [hereinafter referred to as Compound (10)] were dissolved in 2.5 ml of anhydrous acetonitrile and then thereto was added 0.40 g of molecular sieves 3Å, followed by stirring for 5 hours. Thereto was added 3.4 g of molecular sieves 3Å containing 1.7 g of DMTST at −10° C. to −15° C. and reaction was allowed to proceed for 24 hours at that temperature with stirring. After completion of the reaction, the reaction mixture was filtered through Celite and the filtrate was extracted with addition of dichloromethane. The dichloromethane layer was washed with aqueous sodium carbonate solution and water, dried over anhydrous Na$_2$SO$_4$ and then concentrated under reduced pressure. The resulting syrup was subjected to column chromatography [packing material: Wakogel C-200, eluent: toluene/CH$_3$OH=20/1 and ethyl acetate/n-hexane=1/1] to obtain 0.243 g of Compound (9). Yield: 68%

[α]$_D$= −6.36° (C=2.42, CH$_2$Cl$_2$)

IR $\nu_{max}^{film}$(cm$^{-1}$):
3700–3100 (OH, NH), 3100–2800 (CH), 1750, 1220 (ester), 1660, 1550 (amide), 860, 840 (trimethylsilyl), 710 (phenyl)

NMR (CDCl$_3$—CD$_3$OD) δppm: galactose unit; 8.10–7.39 (m, 5H, OBz), 4.99 (dd, 1H, J$_{2,3}$=10.07 Hz, J$_{3,4}$=3.30 Hz, H-3), 4.38 (d, 1H, J$_{1,2}$=7.88 Hz, H-1), 4.15 (d, 1H, H-4), 1.04 (m, 2H, —OCH$_2$CH$_2$Si), 0 (S, 9H, Me$_3$Si). Sialic acid unit; 5.33–5.24 (m, 2H, H-7, H-8), 4.76 (ddd, 1H, J$_{3e,4}$=4.68 Hz, H-4), 4.36 (dd, 1H, J$_{8,9}$=2.57 Hz, J$_{9,9'}$=12.09 Hz, H-9), 2.56 (dd, 1H, J$_{3e,3a}$=12.73 Hz, H-3e), 2.10, 2.08, 1.98, 1.93, 1.82 (5s, 15H, OAcx4, NHAc)

REFERENCE EXAMPLE 8

Preparation of 2-(trimethylsilyl)ethyl O-[methyl(5-acetamido-4,7,8,9-tetra-O-acetyl-3,5-dideoxy-D-glycero-α-D-galacto-2-nonulopyranosyl)onate]-(2→6)-2,4-di-O-acetyl-3-O-benzoyl-β-D-galactopyranoside [Compound of the formula [I] wherein R=acetyl group, R$^1$=methyl group, R$^2$=acetyl group, R$^3$=benzoyl group and TAS=trimethylsilyl group, which is hereinafter referred to as Compound (11)]

0.200 g of Compound (9) obtained in Reference Example 7 was dissolved in 6 ml of anhydrous pyridine and 4 ml of acetic anhydride was added thereto and the mixture was left to stand overnight to allow reaction to proceed. After termination of the reaction, methanol was added to the reaction mixture to decompose excess acetic anhydride, followed by concentration under reduced pressure. The resulting syrup was subjected to column chromatography [packing material: Wakogel C-200, eluent: CH$_2$Cl$_2$/CH$_3$OH=80/1] to quantitatively obtain Compound (11).

[α]$_D$= −7.17° (C=1.70, CHCl$_3$)

IR $\nu_{max}^{film}$(cm$^{-1}$):
3700–3100 (NH), 3100–2800 (CH), 1750, 1220 (ester), 860, 840 (trimethylsilyl), 710 (phenyl).

NMR (CDCl$_3$) δppm: galactose unit; 7.92–7.36 (m, 5H, OBz), 5.62 (broad d, 1H, J$_{3,4}$=2.39 Hz, H-4), 5.35 (dd, 1H, J$_{1,2}$=7.87 Hz, J$_{2,3}$=10.44 Hz, H-2), 5.22 (dd, 1H, J$_{3,4}$=3.48 Hz, H-3), 4.62 (d, 1H, J$_{1,2}$=7.88 Hz, H-1), 3.81 (dd, 1H, J$_{5,6}$=5.87 Hz, J$_{6,6'}$=10.26 Hz, H-6), 3.41 (dd, 1H, J$_{5,6'}$=7.79 Hz, H-6'). Sialic acid unit; 5.39–5.20 (m, 3H, H-7, H-8, NH), 4.83 (ddd, 1H, J$_{3e,4}$=4.58 Hz, H-4), 4.33 (dd, 1H, J$_{8,9}$=2.66 Hz, J$_{9,9'}$=12.64 Hz, H-9), 3.75 (s, 3H, —COOMe), 2.50 (dd, 1H, J$_{3e,3a}$=12.82 Hz, H-3e), 2.17, 2.10, 2.06, 2.01, 1.98, 1.96, 1.86 (7s, 21H, OAcx6, NHAc), 0.94 (m, 2H, —OCH$_2$CH$_2$Si), 0 (s, 9H, Me$_3$Si).

REFERENCE EXAMPLE 9

Preparation of 2-(trimethylsilyl)ethyl O-[methyl(5-acetamido-4,7,8,9-tetra-O-acetyl-3,5-dideoxy-D-glycero-α-D-galacto-2-nonulopyranosyl)onate]-(2→3)-6-O-benzoyl-β-D-galactopyranoside [hereinafter referred to as Compound (12)].

0.43 g of Compound (10) and 0.16 g of Compound (5) obtained in Reference Example 5 were dissolved in 2.5 ml of anhydrous acetonitrile and thereto was added 0.40 g of molecular sieves 3Å, followed by stirring for 5 hours. Thereto was added 3.4 g of molecular sieves 3Å containing 1.7 g of DMTST at $-10°$ C. to $-15°$ C. and reaction was allowed to proceed for 24 hours at the same temperature with stirring. After termination of the reaction, the reaction mixture was filtered through Celite and the filtrate was extracted with addition of dichloromethane. The dichloromethane layer was washed with aqueous sodium carbonate solution and water, dried over anhydrous $Na_2SO_4$ and concentrated under reduced pressure. The resulting syrup was subjected to column chromatography [packing material: Wakogel C-200, eluent: ethyl acetate/n-hexane=1/1 and $CH_2Cl_2/CH_3OH=60/1$] to obtain 0.143 g of Compound (12). Yield: 40%.

$[\alpha]_D = -5.98°$ (C=2.04, $CHCl_3$)

IR $\nu_{max}^{film}$ (cm$^{-1}$);
3700–3150 (OH, NH), 3150–2700 (CH), 1750, 1230 (ester), 1670, 1550 (amide), 860, 840 (trimethylsilyl), 720 (phenyl).

NMR ($CDCl_3$—$CD_3OD$) δ ppm: galactose unit; 8.07–7.29 (m, 5H, OBz), 1.00 (m, 2H, —OCH$_2$CH$_2$Si), O (s, 9H, Me$_3$Si). Sialic acid unit; 4.88 (m, 1H, H-4), 3.77 (s, 3H, COOMe), 2.60 (m, 1H, H-3e).

REFERENCE EXAMPLE 10

Preparation of 2-(trimethylsilyl)ethyl O-[methyl-(5-acetamido-4,7,8,9-tetra-0-acetyl-3,5-dideoxy-D-glycero-α-D-galacto-2-nonulpopyranosyl)onate]-(2→3)-2,4-di-O-acetyl-6-O-benzoyl-β-D-galactopyranoside (compound of the formula [II] where R=acetyl group, R$^1$=methyl group, R$^2$=acetyl group, R$^4$=benzoyl group and TAS=trimethylsilyl group, which is herinafter referred to as Compound (13)).

Compound (12) obtained in Reference Example 9 was acetylated in the same manner as acetylation of Compound (9) in Reference Example 8 and subjected to column chromatography in the same manner as in Reference Example 8 to quantitatively obtain Compound (13).

$[\alpha]_D = -24.51°$ (C=2.66, $CHCl_3$)

IR $\nu_{max}^{film}$ (cm$^{-1}$);
3700–3100 (NH), 3100–2700 (CH), 1750, 1230 (ester), 1660, 1540 (amide), 860, 840 (trimethylsilyl), 720 (phenyl).

NMR ($CDCl_3$—$CD_3OD$) δ ppm: galactose unit; 8.04–7.43 (m, 5H, OBz), 0.98 (m, 2H, —OCH$_2$CH$_2$Si), O (s, 9H, Me$_3$Si). Sialic acid unit; 4.85 (m, 1H, H-4), 3.77 (s, 3H, —COOMe), 2.59 (m, 1H, H-3e), 2.22–1.83 (m, 21H, OAcx6, NHAc).

REFERENCE EXAMPLE 11

Preparation of 2-(trimethylsilyl)ethyl O-[methyl(5-acetamido-4,7,8,9-tetra-O-acetyl-3,5dideoxy-D-glycero-α-D-galacto-2-nonulopyranosyl)onate[-(2→3)-O-(6-O-benzoyl-β-D-galactopyranosyl)-(1→4)-2,6-di-O-benzoyl-β-D-glucopyranoside [hereinafter referred to as Compound (14)].

0.21 g of Compound (10) and 0.15 g of Compound (8) obtained in Reference Example 6 were dissolved in 2.0 ml of anhydrous acetonitrile and then thereto was added 0.30 g of molecular sieves 3Å, followed by stirring overnight. Thereto was added 1.14 g of molecular sieves 3Åcontaining 0.68 g of DMTST at $-10°$ C. to $-15°$ C. and reaction was allowed to proceed for 24 hours at that temperature with stirring. After completion of the reaction, the reaction mixture was filtered through Celite and the filtrate was extracted with addition of dichloromethane. The dichloromethane layer was washed with aqueous sodium carbonate solution and water, dried over anhydrous $Na_2SO_4$ and concentrated under reduced pressure. The resulting syrup was subjected to column chromatography [packing material: Wakogel C-200 eluent: ethyl acetate/n-hexane=4/1] to obtain 0.097 g of Compound (14). Yield: 40%. $[\alpha]_D = +10.9°$ (C=1.74, $CHCl_3$)

IR $\nu_{max}^{film}$ (cm$^{-1}$);
3700–3100 (OH, NH), 3100–2700 (CH), 1730, 1220 (ester), 1650, 1540 (amide), 850, 830 (trimethylsilyl), 710 (phenyl).

NMR ($CDCl_3$—$CD_3OD$) δ ppm: lactose unit; 8.20–7.46 (m, 15H, OBzx3), 5.36 (dd, 1H, $J_{1,2}=8.24$ Hz, $J_{2,3}=9.52$ Hz, H-2), 5.09 (dd, 1H, $J_{gem}=10.26$ Hz, H-6), 4.83 (dd, 1H, $J_{gem}=11.91$, $J_{5,6}=3.30$ Hz, H-6), 4.77 (d, 1H, $J_{1,2}=8.06$ HZ, H-1), 4.72 (d, 1H, $J_{1,2}=7.69$ Hz, H-1'), 4.62 (dd, 1H, $J_{gem}=11.91$Hz, $J_{5,6}=5.86$ Hz, H-6), 3.69 (ddd, 1H, —CHCH$_2$Si), 0.98 (m, 2H, —CH$_2$CH$_2$Si), 0 (s, 9H, Me$_3$Si). Sialic acid unit; 5.42 (m, 2H, H-7, H-8), 4.97 (ddd, 1H, H-4), 3.92 (s, 3H, —COOMe), 2.81 (dd, 1H, $J_{3e,4}=4.49$ Hz, $J_{3e,3a}=12.73$ Hz, H-3e), 2.31–1.99 (5s, 15H, OAcx4, NHAc).

REFERENCE EXAMPLE 12

Preparation of 2-(trimethylsilyl)ethyl O-[methyl(5-acetamido-4,7,8,9-tetra-O-acetyl-3,5-dideoxy-D-glycero-α-D-galacto-2-nonulopyranosyl)onate]-(2→3)-O-(2,4-di-O-acetyl-6-O-benzoyl-β-D-galactopyranosyl)-(1→4)-3-O-acetyl-2,6-di-O-benzoyl-β-D-glucopyranoside [compound of the formula [III] where R=acetyl group, R$^1$=methyl group, R$^5$=acetyl group, R$^6$=benzoyl group and TAS=trimethylsilyl group, which is hereinafter referred to as Compound (15)].

85 mg of Compound (14) obtained in Reference Example 11 was dissolved in 8 ml of anhydrous pyridine and thereto was added 4 ml of acetic anhydride. This was left to stand overnight to allow reaction to proceed. After termination of the reaction, methanol was added to decompose excess acetic anhydride and the reaction mixture was concentrated under reduced pressure. The resulting syrup was subjected to column chromatography [packing material: Wakogel C=200, eluent:

$CH_2Cl_2/CH_3OH=60/1$] to obtain 87 mg of Compound (15). Yield: 94%. $[\alpha]_D= +5.74°$ (C=1.74, $CHCl_3$)

IR $\nu_{max}^{film}$ (cm$^{-1}$);
3700–3200 (NH), 3100–2800 (CH), 1750, 1230 (ester), 1660, 1540 (amide), 860, 840 (trimethylsilyl), 720 (phenyl).

NMR ($CDCL_3$—$CD_3OD$) δ ppm: lactose unit; 8.18–7.50 (m, 15H, Bzx3), 5.59 (t, 1H, $J_{2,3}=J_{3,4}=9.71$ Hz, H-3), 5.32 (dd, 1H, $J_{1,2}=7.88$ Hz, H-2), 5.13 (dd, 1H, $J_{1,2'}=7.87$ Hz, $J_{2',3'}=10.17$ Hz, H-2), 5.13 (d, $J_{3,4}=3.30$, 1H, H-4'), 5.00 (d, 1H, $J_{1,2}=7.88$ Hz, H-1), 4.81 (d, 1H, $J_{1,2}=7.88$ Hz, H-1), 4.74 (dd, 1H, $J_{2',3'}=10.17$Hz, $J_{3',4'}=3.30$ Hz, H-3'), 0.98 (m, 2H, —$CH_2CH_2Si$), 0 (s, 9H, $Me_3Si$). sialic acid unit; 5.64 (m, 1H, H-8), 5.45 (dd, 1H, $J_{7,8}=8.80$ Hz, $J_{6,7}=2.57$ Hz, H-7), 4.94 (ddd, 1H, $J_{3e,4}=4.76$ Hz, H-4), 3.83 (s, 3H, —COOMe), 2.68 (dd, 1H, $J_{3e,3a}=12.64$ Hz, H-3e), 2.35–1.94 (8s, 24H, OAcx7, NHAc).

EXAMPLE 1

Preparation of (2S, 3R, 4E)-1-O-[3-O-(5-acetamido-3,5-dideoxy-D-glycero-α-D-galacto-2-nonulopyranosylonate)-β-D-galactopyranosyl]-2-octadecanamido-4-octadecene-1,3-diol ($GM_4$. compound of the formula [VI] wherein R=acetyl group, R'= —$C_{17}H_{35}$, and n=12, which is hereinafter referred to as Compound (20)). (1) Preparation of O-[methyl(5-acetamido-4,7,8,9-tetra-O-acetyl-3,5-dideoxy-D-glycero-α-D-galacto-2-nonulopyranosyl)onate]-(2→3)-2,4-di-O-acetyl-6-O-benzoyl-D-galactopyranose [hereinafter referred to as Compound (16)].

860 mg of Compound (13) was dissolved in 15 ml of dichloromethane and thereto was added 0.55 ml of $Bf_3$-diethyl ether under ice cooling, followed by stirring at 0° C. for 7 hours. After termination of the reaction, the reaction mixture was extracted with addition of dichloromethane and the dichloromethane layer was washed with aqueous sodium hydrogencarbonate solution and water, dried over anhydrous $Na_2SO_4$ and concentrated under reduced pressure. The resulting syrup was subjected to column chromatography [packing material: Wakogel C-200, eluent: $CH_2Cl_2/CH_3OH=40/1$) to obtain 646 mg of Compound (16). Yield: 84.1%.

$[\alpha]_D= -16.58°$ (C=0.78, $CHCl_3$)

IR $\nu_{max}^{film}$ (cm$^{-1}$);
3700–3150 (NH, OH), 3150–2800 (CH), 1740, 1220 (ester) 1660, 1540 (amide), 710 (phenyl).

(2) Preparation of O-[methyl(5-acetamido-4,7,8,9-tetra-O-acetyl-3,5-dideoxy-D-glycero-α-D-galacto-2-nonulopyranosyl)onate]-(2→3)-2,4-di-O-acetyl-6-O-benzoyl-D-galactopyranosyl trichloroacetoimidate [mixture (1:8) of α compound and β compound, hereinafter referred to as Compound (17)].

645 mg of Compound (16) obtained in (1) was dissolved in 6 ml of dichloromethane and thereto were added 2.4 ml of trichloroacetonitrile and 66 mg of DBU under cooling and reaction was allowed to proceed at 0° C. for 2 hours with stirring. After termination of the reaction, the reaction mixture was concentrated under reduced pressure. The resulting syrup was subjected to column chromatography [packing material: Wakogel C-200, eluent: $CH_2Cl_2/CH_3OH=70/1$] to obtain 705 mg of Compound (17). Yield: 93.3%.

$[\alpha]_D= -6.22°$ (C=0.90, $CHCl_3$)

IR $\nu_{max}^{film}$ (cm$^{-1}$);
3700–3200 (NH), 3200–2800 (CH), 1750, 1220 (ester), 1680, 1550 (amide), 720 (phenyl).

NMR ($CDCl_3$) δ ppm: sialic acid unit; 5.56 (ddd, 1H, H-8), 5.19 (d, 1H, $J_{5,NH}=10.08$Hz, NH), 4.90 (ddd, 1H, $J_{3e,4}=4.76$ Hz, H-4), 4.41 (dd, 1H, $J_{8,9}=2.57$ Hz, $J_{9,9'}=12.46$ Hz, H-9), 4.06 (q, 1H, $J_{5,NH}=J_{4,5}=J_{5,6}=10.44$ Hz, H-5), 3.98 (dd, 1H, $J_{8,9'}=6.05$ Hz, H-9'), 3.78 (s, 3H, COOMe), 3.65 (dd, 1H, $J_{5,6}=10.72$ Hz, $J_{6,7}=2.66$ Hz, H-6), 2.61 (dd, 1H, $J_{3a,3e}=12.73$ Hz, H-3e). galactose unit; 8.69 (s, 1H, C=NH), 8.04–7.40 (m, 5H, OBz), 5.99 (d, 1H, $J_{1,2}=8.24$ Hz, H-1β), 5.34 (dd, 1H, H-2), 5.14 (d, 1H, $J_{3,4}=3.12$ Hz, H-4) 4.80 (dd, 1H, $J_{2,3}=10.26$ Hz, $J_{3,4}=3.30$ Hz, H-3), 2.19, 2.16, 2.14, 2.07, 2.05, 2.01, 1.85 (7s, 21H, OAcx6, NHAc).

(3) Preparation of (2S, 3R, 4E)-1-O-[2,4-di-O-acetyl-6-O-benzoyl-3-O-(methyl 5-acetamido-4,7,8,9-tetra-O-acetyl-3,5dideoxy-D-glycero-α-D-galacto-2-nonulopyranosylonate)-β-D-galactopyranosyl]-2-azido-3-O-benzoyl-4-octadecene-1,3-diol (compound of the formula [IX] wherein R=acetyl group, $R^1$=methyl group, $R^2$=acetyl group, $R^4$=benzoyl group, $R^7$=benzoyl group, $R^8$=-$N_3$ and n=12, which is referred to as Compound (18) hereinafter).

690 mg of Compound (17) obtained in (2) and 600 mg of (2S, 3R, 4E)-2-azido-3-O-benzoyl-4-octadecene-1,3-diol (hereinafter referred to as Compound (A)) were dissolved in 15 ml of dichloromethane and thereto was added 7.0 g of Molecular Sieves 4Å, followed by stirring at room temperature for 30 minutes. Then, thereto was added 200 mg of $BF_3$-diethyl ether under ice cooling and reaction was allowed to proceed at 0° C. for 4 hours with stirring. After termination of the reaction, the reaction mixture was filtered through Celite and the filtrate was extracted with dichloromethane. The dichloromethane layer was washed with aqueous sodium hydrogencarbonate solution and water in sequence, dried over anhydrous $Na_2SO_4$ and concentrated under reduced pressure. The resulting syrup was subjected to column chromatography (packing material: Wakogel C-200, eluent: ethyl acetate/n-hexane=3/2) to obtain 722 mg of Compound (18). Yield: 82.3%.

$[\alpha]_D= -25.60°$ (C=0.58, $CHCl_3$)

IR $\nu_{max}^{film}$ (cm$^{-1}$);
3700–3150 (NH), 3150–2800 (CH), 2100 ($N_3$), 1750, 1220 (ester), 1660, 1540 (amide), 710 (phenyl).

NMR ($CDCl_3$) δ ppm: sialic acid unit; 5.39 (dd, 1H, $J_{6,7}=2.57$ Hz, $J_{7,8}=9.07$ Hz, H-7), 5.19 (d, 1H, $J_{5,NH}=10.26$ Hz, NH), 4.90 (ddd, 1H, $J_{3e,4}=4.67$ Hz, H-4), 3.64 (dd, 1H, $J_{5,6}=10.72$ Hz, H-6), 2.60 (dd, 1H, $J_{3a,3e}=12.73$ Hz, H-3e), 1.72 (t, 1H, $J_{3a,3e}=12.64$ Hz, H-3a). galactose unit; 8.07–7.39 (m, 10H, OBzx2), 5.10 (dd, 1H, $J_{1,2}=8.06$ Hz, $J_{2,3}=10.07$ Hz, H-2), 5.06 (broad d, 1H, $J_{3,4}=3.66$ Hz, H-4), 4.71 (d, 1H, H-1), 4.62 (dd, 1H, $J_{3,4}=3.39$ Hz, H-3), 2.25, 2.13, 2.12, 2.09, 2.03, 2.01, 1.86 (7s, 21H, OAcx6, NHAc). ceramide unit; 5.94 (dt, 1H, $J_{4,5}=14.47$ Hz, $J_{5,6}=J_{5,6'}=6.96$ Hz, H-5), 1.23 (m, 22H, —(CH$_2$)$_{11}$—).

(4) Preparation of (2S, 3R, 4E)-1-O-[2,4-di-O-acetyl-6-O-benzoyl-3-O-(methyl 5-acetamido-4,7,8,9-tetra-O-acetyl-3,5-dideoxy-D-glycero-α-D-galacto-2-nonulopyranosylonate)-β-D-galactopyranosyl]-3-O-benzoyl-2-octadecanamido-4-octadecene-1,3-diol (compound of the formula [IX] wherein R=acetyl group, R$^1$=methyl group, R$^2$=acetyl group, R$^4$=benzoyl group, R$^7$=benzoyl, R$^8$=—NHCOC$_{17}$H$_{35}$ and n=12, which is referred to as Compound (19) hereinafter).

1.30 mg of Compound (18) obtained in (3) was dissolved in 12 ml of a mixed solvent pyridine-water (5:1) and reaction was allowed to proceed for 2 days at room temperature with blowing hydrogen sulfide gas thereinto. After termination of the reaction, the reaction mixture was concentrated under reduced pressure. The resulting —NH$_2$ compound was sufficiently dried and then dissolved in 6 ml of dichloromethane. To the solution were added 59 mg of stearic acid and 60 mg of WSC and reaction was allowed to proceed overnight at room temperature with stirring. After termination of the reaction, the reaction mixture was extracted with addition of dichloromethane and the dichloromethane layer was washed with water, dried over anhydrous Na$_2$SO$_4$ and then concentrated under reduced pressure. The resulting syrup was subjected to column chromatography (packing material: Wakogel C-200, eluent: CH$_2$Cl$_2$/CH$_3$OH=80/1) to obtain 125 mg of Compound (19). Yield: 80.6%.

$[\alpha]_D=-12.43°$ (C=2.46, CHCl$_3$)

IR $\nu_{max}^{film}$ (cm$^{-1}$);
3700-3150 (NH), 3150-2800 (CH), 1750, 1230 (ester), 1660, 1540 (amide), 710 (phenyl).

NMR (CDCl$_3$) δ ppm: sialic acid unit; 5.37 (dd, 1H, $J_{6,7}=2.56$ Hz, $J_{7,8}=9.07$ Hz, H-7), 5.20 (d, 1H, $J_{5,NH}=9.90$ Hz, NH), 4.89 (ddd, 1H, $J_{3e,4}=4.58$ Hz, H-4) 4.36 (dd, 1H, $J_{8,9}=2.56$ Hz, $J_{9,9'}=12.46$ Hz, H-9), 3.75 (s, 3H, COOMe), 3.63 (dd, 1H, $J_{5,6}=10.90$ Hz, H-6), 2.59 (dd, 1H, $J_{3a,3e}=12.46$ Hz, H-3e). galactose unit; 8.04-7.36 (m, 10H,, OBzx2), 5.04 (dd, 1H, H-2), 5.03 (d, 1H, H-4), 4.63 (d, 1H, $J_{1,2}=7.70$ Hz, H-1), 4.61 (dd, 1H, $J_{2,3}=10.07$ Hz, $J_{3,4}=3.30$ Hz, H-3). ceramide unit; 5.88 (d, 1H, $J_{2,NH}=9.34$ Hz, NH), 5.88 (dt, 1H, $J_{4,5}=13.92$ Hz, $J_{5,6}=J_{5,6'}=6.96$ Hz, H-5), 4.49 (m, 1H, H-2), 2.19, 2.12, 2.11, 2.07, 2.03, 2.01, 1.85 (7s, 21H, OAcx6, NHAc).

(5) Preparation of Compound (20)

123 mg of Compound (19) obtained in (4) was dissolved in 5 ml of methanol. To the solution were added three drops of 28% methanolic CH$_3$ONa solution and reaction was allowed to proceed for 12 hours at room temperature. Then, 0.7 ml of water was added to the reaction mixture and reaction was allowed to proceed for further 10 hours at room temperature with stirring. After termination of the reaction, the reaction mixture was neutralized with a cation exchange resin Amberlite IR-120 and filtered. The filtrate was concentrated under reduced pressure. The resulting crystal was washed with large amounts of ether and n-hexane to obtain 75 mg of Compound (20). Yield: 89.3%.

$[\alpha]_D=+2.00°$ (C=0.300, CH$_3$OH)

IR $\nu_{max}^{nujol}$ (cm$^{-1}$);
3700-2500 (OH), 3000-2800 (CH$_2$), 1640, 1560 (amide).

NMR (CDCl$_3$—CD$_3$OD) δ ppm: sialic acid unit; 2.87 (dd, 1H, H-3e), 2.01 (s, 3H, NHAc).galactose unit; 4.29 (d, 1H, $J_{1,2}=7.70$ Hz, H-1). ceramide unit; 5.66 (dt, 1H, $J_{4,5}=14.39$ Hz, $J_{5,6}=J_{5',6'}=7.39$ Hz, H-5), 5.44 (dd, 1H, $J_{4,5}=15.30$ Hz, $J_{3,4}=7.60$ Hz, H-4), 4.23 (dd, 1H, $J_{1,2}=4.21$ Hz, $J_{1,1'}=10.44$ Hz, H-1), 4.10 (t, 1H, $J_{2,3}=J_{3,4}=8.06$ Hz, H-1), 2.18 (t, 2H, J=7.15 Hz, —COC$\underline{H}_2$CH$_2$), 0.89 (t, 6H, J=5.59 Hz, —CH$_2$C$\underline{H}_3$x2).

EXAMPLE 2

Preparation of (2S, 3R, 4E)-1-O-[3-O-(5-acetamido-3,5-dideoxy-D-glycero-α-D-galacto-2-nonulopyranosylonate)-β-D-galactopyranosyl]-2-tetradecanamido-4-octadecene-1,3-diol(GM$_4$, the compound of the formula [IV] where R=acetyl group, R'=-C$_{13}$H$_{27}$, an n-12, hereinafter referred to as Compound (22)).

(1) Preparation of (2S, 3R, 4E)-1-O-[2,4-di-O-acetyl-6-O-benzoyl-3-O-(methyl 5-acetamido-4,7,8,9-tetra-O-acetyl-3,5-dideoxy-D-glycero-α-D-galacto-2-nonulpopyranosylonate)-β-D-galactopyranosyl]-3-O-benzoyl-2-tetradecanamido-4-octadecene-1,3-diol (compound of the formula [IX] where R=acetyl group, R$^1$=methyl group, R$^2$=acetyl group, R$^4$=benzoyl group, R$^7$=benzoyl group, R$^8$=NHCOC$_{13}$H$_{27}$ and n=12, referred to as Compound (21) hereinafter).

130 mg of Compound (18) obtained in (3) of Example 1was dissolved in 12 ml of a mixed solvent of pyridine-water (5:1) and reaction was allowed to proceed for 2 days at room temperature with blowing hydrogen sulfide gas thereinto. After termination of the reaction, the reaction mixture was concentrated under reduced pressure. The resulting —NH$_2$ compound was sufficiently dried and then dissolved in 5 ml of dichloromethane. To the solution were added 47 mg of myristic acid and 60 mg of WSC and reaction was allowed to proceed overnight at room temperature with stirring. After termination of the reaction, the reaction mixture was extracted with addition of dichloromethane and the dichloromethane layer was washed with water, dried over anhydrous Na$_2$SO$_4$ and then concentrated under reduced pressure. The resulting syrup was subjected to column chromatography (packing material: Wakogel C-200, eluent: CH$_2$Cl$_2$/CH$_3$OH=80/1) to obtain 119 mg of Compound (21). Yield: 79.9%.

$[\alpha]_D=-13.62°$ (C=2.32, CHCl$_3$)

IR $\nu_{max}^{film}$ (cm$^{-1}$);
3700-3150 (NH), 3150-2800 (CH), 1740, 1220 (ester), 1650, 1540 (amide), 710 (phenyl).

NMR (CDCl$_3$) δ ppm: sialic acid unit; 5.37 (dd, 1H, $J_{6,7}=2.56$, $J_{7,8}=9.16$ HZ, H-7), 5.16 (d, 1H, $J_{5,NH}=10.26$ Hz, NH), 4.89 (ddd, 1H, H-4), 4.35 (dd, 1H, $J_{8,9}=2.56$ Hz, $J_{9,9'}=12.64$ Hz, H-9), 3.75 (s, 3H, COOMe), 3.62 (dd, 1H, $J_{5,6}=10.72$ Hz, H-6), 2.59 (dd, 1H, $J_{3e,4}=4.58$ Hz, $J_{3e,3a}=12.64$ Hz, H-3e), 1.75 (t, 1H, $J_{3a,3e}=J_{3a,4}=11.91$ Hz, H-3a). galactose unit; 8.04–7.36 (m, 10H, OBzx2), 5.04 (dd, 1H, H-2), 5.03 (d, 1H, H-4), 4.63 (d, 1H, $J_{1,2}=8.06$ Hz, H-1), 4.60(dd, 1H, $J_{2,3}=10.17$ Hz, $J_{3,4}=3.21$ Hz, H-3). ceramide unit; 5.88 (dt, 1H, $J_{4,5}=14.02$ Hz, $J_{5,6}=J_{5,6'}=7.01$ Hz, H-5), 5.87 (d, 1H, $J_{2,NH}=9.53$ Hz, NH), 4.50 (m, 1H, H-2).

(2) Preparation of Compound (22)

116 mg of Compound (21) obtained in (1) was dissolved in 5 ml of methanol. To the solution were added four drops of 28% methanolic CH3ONa solution and reaction was allowed to proceed for 8 hours at room temperature. Then, 0.5 ml of water was added to the reaction mixture and reaction was allowed to proceed for further 3 hours at room temperature with stirring. After termination of the reaction, the reaction mixture was neutralized with Amberlite IR-120 and filtered. The filtrate was concentrated to dryness under reduced pressure to quantitatively obtain Compound (22).

$[\alpha]_D = +2.28°$ (C=0.35, CH3OH)

IR $\nu_{max}^{nujol}$ (cm$^{-1}$);
3700–2500 (OH), 3000–2800 (CH2), 1640, 1560 (amide)

NMR (CDCl3—CD3OD) δ ppm: sialic acid unit; 2.88 (dd, 1H, $J_{3e,4}=3.85$ Hz, H-3e), 2.01 (s, 3H, NHAc). galactose unit; 4.28 (d, 1H, $J_{1,2}=7.88$ Hz, H-1). ceramide unit; 5.68 (dt, 1H, $J_{4,5}=14.11$ Hz, $J_{5,6}=J_{5,6'}=7.05$ Hz, H-5), 5.44 (dd, 1H, $J_{4,5}=15.57$ Hz, $J_{3,4}=7.33$ Hz, H-4), 4.21 (dd, 1H, $J_{1,2}=4.03$ Hz, $J_{1,1'}=10.07$ Hz, H-1), 4.10 (t, 1H, $J_{2,3}=J_{3,4}=8.15$ Hz, H-3), 3.68 (t, 2H, J=7.42 Hz, —COCH2CH2), 0.90 (t, 6H, J=6.69 Hz, —CH2C$\underline{H}$3x2)

EXAMPLE 3

Preparation of (2S, 3R, 4E)-1-O-[6-O-(5-acetamido-3,5-dideoxy-D-glycero-α-D-galacto-2-nonulopyranosylonate)-β-D-galactopyranosyl]-2-octadecanamido-4-octadecene-1,3-diol (position isomer of GM4. compound of the formula [V] wherein R=acetyl group, R'=—C17H35, and n=12, which is hereinafter referred to as Compound (27)).

(1) Preparation of O-[methyl(5-acetamido-4,7,8,9-tetra-O-acetyl-3,5-dideoxy-D-glycero-α-D-galacto-2-nonulopyranosylonate]-(2→6)-2,3,4-tri-O-acetyl-D-galactopyranose [hereinafter referred to as Compound (23)].

495 mg of 2-(trimethylsilyl)ethyl O-[methyl(5-acetamido-4,7,8,9-tetra-O-acetyl-3,5-dideoxy-D-glycero-α-D-galacto-2-nonulopyranosyl)onate]-(2→6)-2,3,4-tri-O-acetyl-β-D-galactopyranoside (compound of the formula [I] wherein R=acetyl group, R$^1$=methyl group, R$^2$=R$^3$=acetyl group and TAS=-trimethylsilyl group) was dissolved in 10 ml of dichloromethane and thereto was added dropwise 340 mg of BF3-diethyl ether under ice cooling and reaction was allowed to proceed at 0° C. - room temperature for 3 hours. After termination of the reaction, the reaction mixture was extracted with addition of dichloromethane and the dichloromethane layer was washed with aqueous sodium hydrogencarbonate solution and water, dried over anhydrous Na2SO4 and concentrated under reduced pressure. The resulting syrup was subjected to column chromatography [packing material: Wakogel C-200, eluent: CH2Cl2/CH3OH=60/1) to obtain 403 mg of Compound (23). Yield: 91.8%.

$[\alpha]_D = +0.25°$ (C=0.79, CHCl3)

IR $\nu_{max}^{film}$ (cm$^{-1}$);
3700–3100 (NH, OH), 3100–2800 (CH), 1750, 1230 (ester), 1670, 1550 (amide).

NMR (CDCl3) δ ppm: sialic acid unit; 5.38 (ddd, 1H, $J_{8,9}=2.57$ Hz, $J_{7,8}=7.52$ Hz, H-8), 4.88 (ddd, 1H, $J_{3e,4}=4.58$ Hz, H-4), 4.37 (dd, 1H, $J_{8,9}=2.57$ Hz, $J_{9,9'}=12.28$ Hz, H-9), 4.02 (dd, 1H, $J_{8,9'}=7.70$ Hz, H-9'), 3.79 (s, 3H, —COOMe), 2.54 (dd, 1H, $J_{3a,3e}=13.10$ Hz, H-3e). galactose unit; 5.54 (broad d, 1H, $J_{3,4}=2.38$ Hz, H4), 5.47 (dd, 1H, $J_{2,3}=10.44$ Hz, $J_{3,4}=3.30$ Hz, H-3), 3.69 (dd, 1H, $J_{5,6}=5.50$ Hz, $J_{6,6'}=10.62$ Hz, H-6), 3.41 (dd, 1H, $J_{5,6'}=8.98$ Hz, H-6').

(2) Preparation of O-[methyl(5-acetamido-4,7,8,9-tetra-O-acetyl-3,5-dideoxy-D-glycero-α-D-galacto-2-nonulopyranosyl)onate]-(2→6)-2,3,4-tri-O-acetyl-D-galactopyranosyl trichloroacetoimidate [mixture (11:1) of α compound and β compound, referred to as Compound (24) hereinafter].

315 mg of Compound (23) obtained in (1) was dissolved in 3 ml of dichloromethane and thereto were added 0.83 ml of trichloroacetonitrile and 32 mg of DBU under cooling and reaction was allowed to proceed at 0° C. for 2 hours with stirring. After termination of the reaction, the reaction mixture was concentrated under reduced pressure. The resulting syrup was subjected to column chromatography [packing material: Wakogel C-200, eluent: CH2CL2/CH3OH=50/1] to obtain 344 mg of Compound (24). Yield: 92.2%

$[\alpha]_D = +38.40°$ (C=0.50, CHCl3)

IR $\nu_{max}^{film}$ (cm$^{-1}$);
3700–3200 (NH), 3200–2800 (CH), 1750, 1220 (ester), 1680, 1540 (amide).

NMR (CDCl3) δ ppm: sialic acid unit: 4.86 (m, 1H-4), 4.25 (dd, 1H, $J_{8,9}=2.38$ Hz, $J_{9,9'}=12.46$ Hz, H-9), 4.09 (dd, 1H, $J_{8,9'}=4.67$ Hz, H-9'), 3.78 (s, 3H, COOMe), 2.52 (dd, 1H, $J_{3a,3e}=12.92$ Hz, $J_{3e,4}=4.67$ Hz, H-3e). galactose unit; 8.66 (s, 1H, C=NH), 6.61 (d, 1H, $J_{1,2}=3.11$ Hz, H-1a), 4.86 (broad d, 1h, H-4), 4.34 (broad t, 1H, $J_{5,6}=6.23$ Hz, H-5), 3.91 (dd, 1H, $J_{5,6}=6.05$ Hz, $J_{6,6}=10.08$ Hz, H-6), 3.33 (dd, 1H, $J_{5,6}=6.51$ Hz, H-6'), 2.18, 2.15, 2.10, 2.04, 2.02, 2.01, 1.87 (7s, 24H, OAcx7, NHAc).

(3) Preparation of (2S, 3R, 4E)-1-O-[2,3,4-tri-O-acetyl-6-O-(methyl 5-acetamido-4,7,8,9-tetra-O-acetyl-3,5-dideoxy-D-glycero-α-D-galacto-2nonulopyranosylonate)-β-D-galactopyranosyl]-2azido-3-O-benzoyl-4-octadecene-1,3-diol (compound of the formula [VIII] wherein R=acetyl group, R$^1$=methyl group, R$^2$=R$^3$=acetyl group, R$^7$=benzoyl group, R$^8$=—N3 and n=12, which is referred to as Compound (25) hereinafter).

341 mg of Compound (24) obtained in (2) and 317 mg of Compound (A) were dissolved in 7 ml of dichloromethane and thereto was added 3.50 g of Molecular Sieves 4Å, followed by stirring at room temperature for 30 minutes. Then, thereto was added 107 mg of BF3- diethyl ether under ice cooling and reaction was allowed to proceed at 0° C.–15° C. for 4 hours with stirring. After termination of the reaction, the reaction mixture was filtered through Celite and the filtrate was extracted with dichloromethane. The dichloromethane layer was washed with aqueous sodium hydrogencarbonate solution and water in sequence, dried over anhydrous $Na_2SO_4$ and concentrated under reduced pressure. The resulting syrup was subjected to column chromatography (packing material: Wakogel C-200, eluent: ethyl acetate/n-hexane=3/2) to obtain 227 mg of Compound (25). Yield: 51.6%. $[\alpha]=-19.42°$ (C=2.42, $CHCl_3$)

---
IR $\nu_{max}^{film}$ ($cm^{-1}$);
3700–3200 (NH), 3100–2800 (CH), 2100 ($N_3$),
1750, 1220 (ester), 1660, 1540 (amide), 710 (phenyl).

---

NMR ($CDCl_3$) δ ppm: sialic acid unit: 4.85 (m, 1H, H-4), 4.33 (dd, 1H, $J_{9,9'}$=12.27 Hz, H-9), 2.52 (dd, 1H, $J_{3a,3e}$=12.73 Hz, $J_{3e,4}$=4.49 Hz, H-3e). galactose unit; 5.46 (broad d, 1H, H-4), 5.22 (dd, 1H, $J_{1,2}$=7.88 Hz, $J_{2,3}$=10.45 Hz, H-2), 5.07 (dd, 1H, $J_{3,4}$=3.30 Hz, H-3), 4.61 (d, 1H, $J_{1,2}$=7.70 Hz, H-1). ceramide unit; 8.08–7.43 (m, 5H, OBz), 5.93 (dt, 1H, $J_{4,5}$=14.02 Hz, $J_{5,6}$=$J_{5,6'}$=7.01 Hz, H-5), 1.25 (m, 22H, —($CH_2$)$_{11}$—Me), 2.19, 2.15, 2.11, 2.11, 2.03, 2.02, 1.98 1.88 (8s, 24H, OAcx7, NHAc).

(4) Preparation of (2S, 3R, 4E)-1-O-[2,3,4-tri-O-acetyl-6-O-(methyl 5-acetamido-4,7,8,9-tetra-O-acetyl-3,5-dideoxy-D-glycero-α-D-galacto-2-nonulopyranosylonate)-β-D-galactopyranosyl]-3-O-benzoyl-2-octadecanamido-4-octadecene-1,3-diol (compound of the formula [VIII] wherein R=acetyl group, $R^1$methyl group, $R^2$=$R^3$=acetyl group, $R^7$=benzoyl group, $R^8$=$NHCOC_{17}H_{35}$ and n=12, which is referred to as Compound (26) hereinafter).

102 mg of Compound (25) obtained in (3) was dissolved in 12 ml of a mixed solvent pyridine-water (5:1) and reaction was allowed to proceed for 36 hours at room temperature with blowing hydrogen sulfide gas thereinto. After termination of the reaction, the reaction mixture was concentrated under reduced pressure. The resulting —$NH_2$ compound was sufficiently dried and then dissolved in 6 ml of dichloromethane. To the solution were added 58 of stearic acid and 58 mg of WSC and reaction was allowed to proceed overnight at room temperature with stirring. After termination of the reaction, the reaction mixture was extracted with addition of dichloromethane and the dichloromethane layer was washed with water, dried over anhydrous $Na_2SO_4$ and then concentrated under reduced pressure. The resulting syrup was subjected to column chromatography (packing material: Wakogel C-200, eluent: $CH_2Cl_2$/$CH_3OH$=80/1) to obtain 60 mg of Compound (26). Yield:48.8%
$[\alpha]_D=-13.10°$ (C=1.16, $CHCl_3$)

---
IR $\nu_{max}^{film}$ ($cm^{-1}$);
3700–3200 (NH), 3100–2800 (CH), 1750, 1220 (ester), 1660, 1540 (amide), 710 (phenyl).

---

NMR ($CDCl_3$) δ ppm: sialic acid unit; 5.30 (ddd, 1H, $J_{8,9}$=2.38 Hz, H-8), 4.84 (ddd, 1H, $J_{3e,4}$=4.58 Hz, H-4), 4.30 (dd, 1H, $J_{9,9'}$=12.37 Hz, H-9), 3.77 (s, 3H, COOMe), 2.50 (dd, 1H, $J_{3a,3e}$=12.82 Hz, H-3e). galactose unit; 5.45 (broad d, 1H, $J_{3,4}$=3.12 Hz, H-4), 5.15 (dd, 1H, $J_{1,2}$=7.70 Hz, $J_{2,3}$=10.54 Hz, H-2), 5.06 (dd, 1H, H-3), 4.56 (d, 1H, H-1), 3.36 (dd, 1H, $J_{6,6'}$=10.63 Hz, H-6). ceramide unit; 8.05–7.41 (m, 5H, OBz), 5.94 (d, 1H, $J_{2,NH}$=9.16 Hz, NH), 5.87 (dt, 1H, $J_{4,5}$=14.10 Hz, $J_{5,6}$=$J_{5,6'}$=7.05 Hz, H-5), 4.49 (m, 1H, H-2), 1.25 (m, 52H, —($CH_2$)$_{11}$—, —($CH_2$)$_{15}$—).

(5) Preparation of Compound (27)

158 mg of Compound (26) obtained in (4) was dissolved in 5 ml of methanol. To the solution were added four drops of 28% methanolic $CH_3ONa$ solution and reaction was allowed to proceed for 12 hours at room temperature with stirring. Then, 0.5 ml of water was added to the reaction mixture and reaction was allowed to proceed for further 10 hours at room temperature with stirring. After termination of the reaction, the reaction mixture was neutralized with Amberlite IR-120 and filtered. The filtrate was concentrated to dryness under reduced pressure to obtain quantitatively Compound (27).

$[\alpha]_D=+1.00°$ (C=0.80,$CH_3OH$)

---
IR $\nu_{max}^{film}$ ($cm^{-1}$);
3700–2500 (OH), 3000–2800 ($CH_2$), 1640, 1560 (amide).

---

MNR ($CD_3OD$) TMS/$CDCl_3$) δ ppm: sialic acid unit; 2.80 (dd, 1H, $J_{3e,4}$=4.39 Hz, $J_{3e,3a}$=12.36 Hz, H-3e), 2.01 (s, 3H, NHAc). galactose unit; 4.21 (d, 1H, $J_{1,2}$=6.78 Hz, H-1). ceramide unit; 5.68 (dt, 1H, $J_{4,5}$=14.57 Hz, $J_{5,6}$=$J_{5,6'}$=7.28 Hz, H-5), 5.43 (dd, 1H, $J_{4,5}$=15.48 Hz, $J_{3,4}$=7.42 Hz, H-4), 4.15 (dd, 1H, $J_{1,2}$=4.40 Hz, $J_{1,1'}$=10.26 Hz, H-1), 4.06 (t, 1H, $J_{2,3}$=$J_{3,4}$=7.97 Hz, H-3), 2.16 (t, 2H, J=7.51 Hz, —COC$\underline{H_2}$C$H_2$), 0.90 (t, 6H, J=6.32 Hz, —$CH_2$C$\underline{H_3}$×2).

EXAMPLE 4

Preparation of (2S, 3R, 4E)-1-O-]3'-O-(5-acetamido-3,5-dideoxy-D-glycero-α-D-galacto-2-nonulopyranosylonate)-β-D-lactopyranosyl]-2-octadecanamido-4-octadecene-1,3-diol ($GM_3$. compound of the formula [VII] wherein R=acetyl group, R'=—$C_{17}H_{35}$, and n=12, which is hereinafter referred to as Compound (32)).

(1) Preparation of O-[methyl(5-acetamido-4,7,8,9-tetra-O-acetyl-3,5-dideoxy-D-glycero-α-D-galacto-2-nonulopyranosyl)onate]-(2→3)-O-(2,4-O-acetyl-6-O-benzoyl-β-D- galactopyranosyl)-(1→4)
-3-O-acetyl-2,6-di-O-benzoyl-D-glucopyranose (referred to as Compound (28) hereinafter).

666 mg of Compound (15) was dissolved in 10 ml of dichloromethane and thereto was added dropwise 0.5 ml of $BF_3$-diethyl ether under ice cooling and reaction was allowed to proceed for 7 hours at 0° C. ~ room temperature. After termination of the reaction, the reaction mixture was extracted with addition of dichloromethane and the dichloromethane layer was washed with aqueous sodium hydrogencarbonate solution and water, dried over anhydrous $Na_2SO_4$ and concentrated under reduced pressure. The resulting syrup was subjected to column chromatography (packing material:

Wakogel C-200, eluent: CH$_2$Cl$_2$/CH$_3$OH=40/1) to obtain 499 mg of Compound (28). Yield: 80.9%.

[α]$_D$= +40.07 (C=1.03, CHCl$_3$)

IR $\nu_{max}^{film}$ (cm$^{-1}$);
3700–3150 (NH, OH), 3150–2800 (CH), 1740, 1230 (ester), 1660, 1550 (amide), 720 (phenyl).

(2) Preparation of O-[methyl(5-acetamido-4,7,8,9-tetra-O-acetyl-3,5-dideoxy-D-glycero-α-D-galacto-2-nonulopyranosyl)onate]-(2→3)-O-(2,4-di-O-acetyl-6-O-benzoyl-β-D-galactopyranosyl)-(1→4)-(3-O-acetyl-2,6-di-O-benzoyl-α-D-glucopyranosyl)trichloroacetoimidate (referred to as Compound (29) hereinafter).

499 mg of Compound (28) obtained in (1) was dissolved in 3 ml of dichloromethane and thereto were added 1.2 ml of trichloroacetonitrile and 32 mg of DBU under cooling and reaction was allowed to proceed for 0° C. for 2 hours with stirring. After termination of the reaction, the reaction mixture was concentrated under reduced pressure. The resulting syrup was subjected to column chromatography [packing material; Wakogel C-200, eluent: CH$_2$Cl$_2$/CH$_3$OH=70/1] to obtain 522 mg of Compound (29). Yield: 93.9%.

[α]$_D$= +41.84° (C=0.76, CHCl$_3$)

IR $\nu_{max}^{film}$ (cm$^{-1}$);
3700–3150 (NH), 3150–2800 (CH), 1740, 1230 (ester), 1680, 1540 (amide), 720 (phenyl).

NMR (CDCl$_3$) δ ppm: sialic acid unit; 3.71 (s, 3H, COOMe), 2.59 (dd, 1H, J$_{3a,3e}$=13.37 Hz, J$_{3e,4}$=4.76 Hz, H-3e). lactose unit; 8.55 (s, 1H, C=NH), 6.66 (d, 1H, J$_{1,2}$=3.67 Hz, H-1), 8.06–7.43 (m, 15H, OBzx3), 2.21, 2.13, 2.06, 2.04, 2.01, 2.00, 1.97, 1.84 (8s, 24H, OAcx7, NHAc).

(3) Preparation of (2S, 3R, 4E)-1-O-[2', 3, 4', -tri-O-acetyl-2,6,6'-tri-O-benzoyl-3'-O-(methyl 5-acetamido-4,7,8,9-tetra-O-acetyl-3,5-dideoxy-D-glycero-α-D-galacto-2-nonulpyranosylonate)-β-D-lactopyranosyl]-2-azido-3-O-benzoyl-4-octadecene-1,3-diol (compound of the formula [X] wherein R=acetyl group, R$^1$=methyl group, R$^5$=acetyl group, R$^6$=benzoyl group, R$^7$=benzoy group, R$^8$=-N$_3$ and n=12, which is referred to as Compound (30) hereinafter).

504 mg of Compound (29) obtained in (2) and 310 mg of Compound (A)) were dissolved in 10 ml of dichloromethane and thereto was added 6.0 g of molecular sieves 4Å, followed by stirring at room temperature for 30 minutes. Then, thereto was added 104 mg of BF$_3$-diethyl ether under ice cooling and reaction was allowed to proceed at 0° C. for 4 hours with stirring. After termination of the reaction, the reaction mixture was filtered through Celite and the filtrate was extracted with dichloromethane. The dichloromethane layer was washed with aqueous sodium hydrogencarbonate solution and water in sequence, dried over anhydrous Na$_2$SO$_4$ and concentrated under reduced pressure. The resulting syrup was subjected to column chromatography (packing material: Wakogel C-200, eluent: ethyl acetate/n-hexane=3/2) to obtain 552 mg of Compound (30 ). Yield: 92.0%.

[α]$_D$= −2.79° (C=0.57, CHCl$_3$)

IR $\nu_{max}^{film}$ (cm$^{-1}$);
3700–3150 (NH), 3150–2800 (CH), 2100 (N$_3$), 1750, 1230 (ester), 1660, 1540 (amide), 710 (phenyl).

NMR (CDCl$_3$) δ ppm: sialic acid unit; 5.26 (d, 1H, J$_{5,NH}$=10.26 Hz, NH), 4.86 (m, 1H, H-4), 3.71 (s, 3H, COOMe) 2.58 (dd, 1H, J$_{3a,3e}$=12.64 Hz, J$_{3e,4}$=4.58 Hz, H-3e), 1.68 (t, 1H, H-3a). lactose unit; 8.07–7.35 (m, 20H, OBzx4), 5.26 (dd, 1H, J$_{1,2'}$=7.88 Hz, J$_{2,3}$=9.53 Hz, H-2), 5.04 (dd, 1H, J$_{1',2'}$=7.88 Hz, J$_{2',3'}$=10.07 Hz, H-2'), 5.00 (broad d, 1H, H-4'), 4.89 (d, 1H, J$_{1',2'}$=7.88 Hz, H-1), 4.70 (d, 1H, H-1), 4.61 (dd, 1H, J$_{3',4'}$=3.30 Hz, H-4), 2.21, 2.12, 2.03, 2.03, 2.02, 2.00, 1.99, 1.84 (8s, 24H, OAcx7, NHAc). ceramide unit; 5.68 (dt, 1H, J$_{4,5}$=14.11 Hz, J$_{5,6}$=J$_{5,6'}$=7.05 Hz, H-5).

(4) Preparation of (2S, 3R, 4E)-1-O-[2', 3, 4', -tri-O-acetyl-2,6,6'-tri-O-benzoyl-3'-O-(methyl 5-acetamido-4,7,8,9-tetra-O-acetyl-3,5-dideoxy-D-glycero-α-D-galacto-2-nonulopyranosylonate)-β-D-lactopyranosyl]-3-O-benzoyl-2octadecanamido-4-octadecene-1,3-diol (compound of the formula [X] wherein R=acetyl group, R$^1$=methyl group, R$^5$=acetyl group, R$^6$=benzoyl group, R$^7$=benzoyl group, R$^8$=NHCOC$_{17}$H$_{35}$ and n=12, which is referred to as Compound (31) hereinafter).

100 mg of Compound (30) obtained in (3) was dissolved in 12 ml of a mixed solvent pyridine-water (5:1) and reaction was allowed to proceed for 36 hours at room temperature with blowing hydrogen sulfide gas thereinto. After termination of the reaction, the reaction mixture was concentrated under reduced pressure. The resulting —NH$_2$ compound was sufficiently dried and then dissolved in 5 ml of dichloromethane. To the solution were added 34 mg of stearic acid and 36 mg of WSC and reaction was allowed to proceed overnight at room temperature with stirring. After termination of the reaction, the reaction mixture was extracted with addition of dichloromethane and the dichloromethane layer was washed with water, dried over anhydrous Na$_2$SO$_4$ and then concentrated under reduced pressure. The resulting syrup was subjected to column chromatography (packing material: Wakogel C-200, eluent: CH$_2$Cl$_2$/CH$_3$OH=60/1) to obtain 102 Mg of Compound (31). Yield: 89.5%.

[α]$_D$= +9.60° (C=2.04, CHCl$_3$)

IR $\nu_{max}^{film}$ (cm$^{-1}$);
3700–3150 (NH), 3150–2800 (CH), 1740, 1220 (ester), 1660, 1530 (amide), 710 (phenyl).

NMR (CDCl$_3$) δ ppm: sialic acid unit; 5.16 (d, 1H, J$_{5,NH}$=10.26 Hz, NH), 3.71 (s, 3H, COOMe), 2.57 (dd, 1H, J$_{3a,3e}$=12.64 , J$_{3e,4}$=4.77 Hz, H-3e). 1.67 (t, 1H, J$_{3a,3e}$=12.46 Hz, H-3a). lactose unit; 8.06–7.25 (m, 20H, OBzx4), 5.19 (dd, 1H, J$_{1,2}$=7.88 Hz, J$_{2,3}$=9.90 Hz, H-2), 4.84 (d, 1H, J$_{1',2'}$=7.88 Hz, H-1'), 4.61 (d, 1H, J$_{1,2}$=7.88 Hz, H-1), 4.60 (dd, 1H, J$_{3',4'}$=3.66 Hz, H-3'), 5.01 (dd, 1H, J$_{2',3'}$=10.35 Hz, H-2), 5.00 (broad d, 1H, H-4'), 2.18, 2.11, 2.03, 2.02, 2.02, 2.00, 2.00, 1.84 (8s, 24H, OAcx7, NHAc). ceramide unit; 5.77 (dt, 1H, J$_{4,5}$=14.20 Hz, J$_{5,6}$=J$_{5,6'}$=7.10 Hz, H-5), 5.66(d, 1H, J$_{2,NH}$=8.98 Hz, NH).

(5) Preparation of Compound (32)

100 mg of Compound (31) obtained in (4) was dissolved in 5 ml of methanol. To the solution were added three drops of 28% methanolic CH₃ONa solution and reaction was allowed to proceed for 8 hours at room temperature with stirring. Then, 0.5 ml of water was added to the reaction mixture and reaction was allowed to proceed for further 4.5 hours at room temperature with stirring. After termination of the reaction, the reaction mixture was neutralized with a Amberlite IR-120 and filtered. The filtrate was concentrated to dryness under reduced pressure to obtain quantitatively Compound (32).

$[\alpha]_D = +1.53°$ [C=0.26, CHCl₃/CH₃OH=1/1 (v/v)].

---

IR $\nu_{max}^{film}$ (cm⁻¹);
3700–2500 (OH), 3000–2800 (CH₂), 1640, 1560 (amide).

---

NMR (CDCl₃—CD₃OD) δppm: sialic acid unit; 2.85 (dd, 1H, H-3e), 2.02 (s, 3H, NHAc). lactose unit; 4.44 (d, 1H, $J_{1',2'}$=7.87 Hz, H-1'), 4.31 (d, 1H, $J_{1,2}$=8.06Hz, H-1). ceramide unit; 5.69· (dt, 1H, $J_{4,5}$=14.02Hz, $J_{5,6}$=$J_{5,6'}$=7.01Hz, H-5), 5.44 (dd, 1H, $J_{4,5}$=15.39Hz, $J_{3,4}$=7.51Hz, H-4), 4.20 (dd, 1H, $J_{1,2}$=4.31Hz, $J_{1,1'}$=9.99Hz, H-1), 2.20 (t, 2H, J=6.69Hz, —COC$\underline{H_2}$CH₂), 0.89 (t, 6H, J=6.60Hz, —CH₂C$\underline{H_3}$×2).

What is claimed is:

1. A process for producing a ganglioside represented by the following formula [V], [VI] or [VII]:

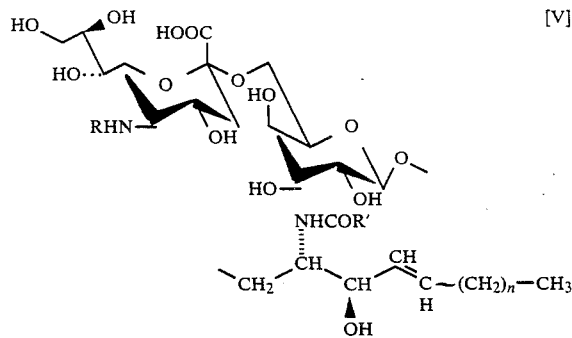

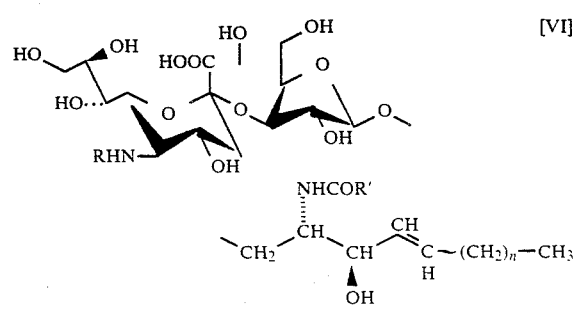

wherein R, R' and n are as defined above,

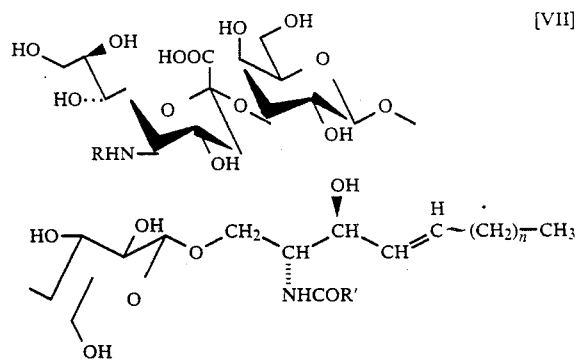

wherein R, R' and n are as defined above, which comprises eliminating the protecting group for hydroxyl group at 1-position of the reducing-end-glucose residue of 2-α-O-glycoside compound of sialic acid represented by the following formula [I], [II] or [III]:

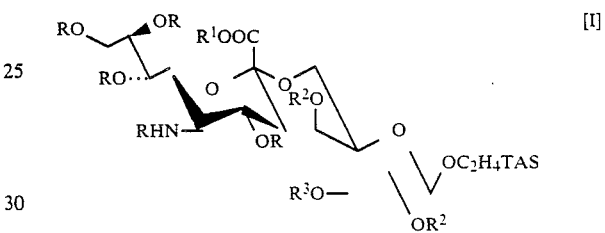

wherein R₁ represents a lower alkyl group, R² and R³ each represents an acyl group and TAS denotes trialkylsilyl group, R is as defined above,

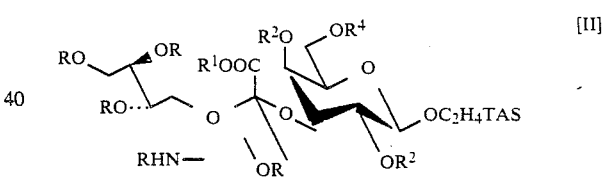

wherein R² and R⁴ each represents an acyl group and R, R¹ and TAS are as defined above,

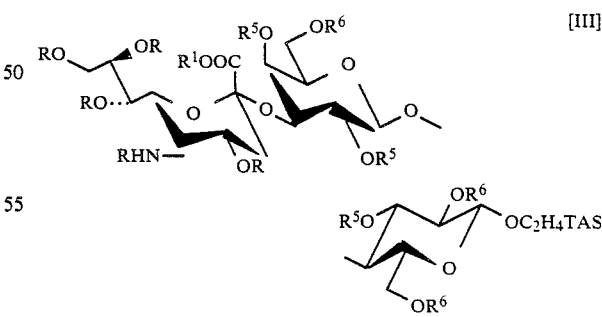

wherein R⁵ and R⁶ each represents an acyl group and R, R¹ and TAS are as defined above, reacting the thus treated compound with trichloroacetonitrile in the presene of a basic catalyst to convert the hydroxyl group at 1-position of the reducing-end-glucose residue to trichloroacetoimide —OC(NH)CCl₃, reacting the product with an azidosphingosine derivative represented by the formula [IV]:

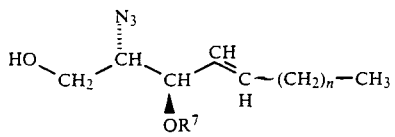

wherein R[7] represents an acyl group and n is as defined above to replace the —OC(NH)CCl$_3$ group at 1-position of the reducing-end-glucose residue with the following group:

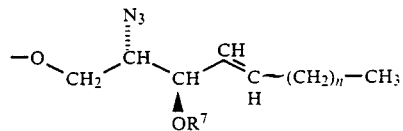

wherein R[7] and n are as defined above, then reducing the product, N-acylating the reduction product with a fatty acid and thereafter successively deprotecting the protecting group for hydroxyl group and protecting group for carboxyl group.

2. A compound represented by the following formula [VIII]:

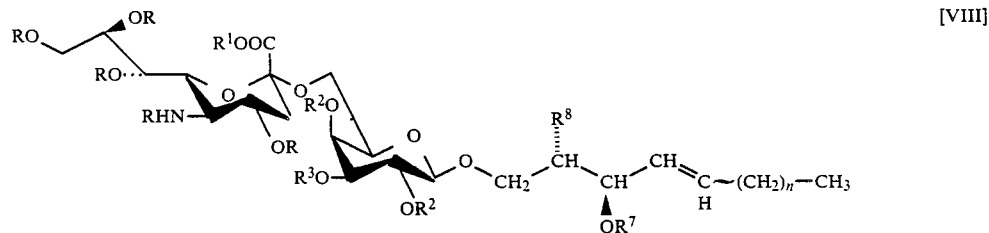

[VIII]

wherein R[8] represents —N$_3$, —NH$_2$ or —NHCOR' where R' is as defined above and R, R[1], R[2], R[3], R[7] and n are as defined above.

3. A compound represented by the formula [IX]:

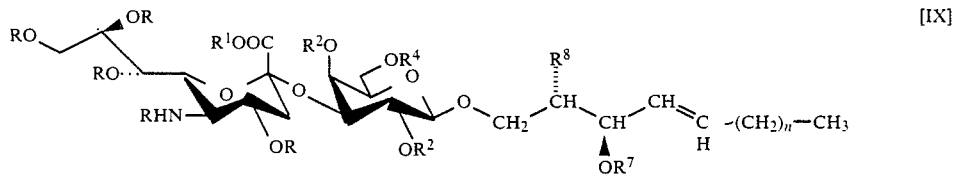

[IX]

wherein R, R[1], R[2], R[4], R[7], R[8] and n are as defined above.

4. A compound represented by the formula [X]:

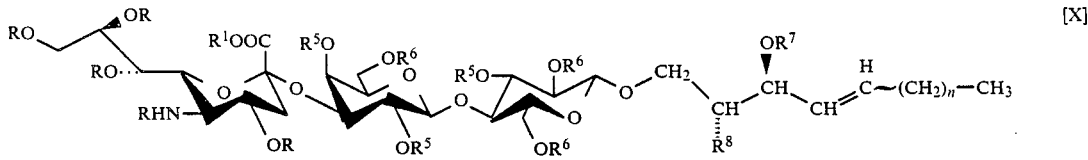

[X]

wherein R, R[1], R[5], R[6], R[7], R[8] and n are as defined above.

* * * * *

UNITED STATES PATENT AND TRADEMARK OFFICE
CERTIFICATE OF CORRECTION

PATENT NO. : 4,918,170
DATED : April 17, 1990
INVENTOR(S) : Akira HASEGAWA et al.

It is certified that error appears in the above-identified patent and that said Letters Patent is hereby corrected as shown below:

Column 2, Formula (VI), delete "

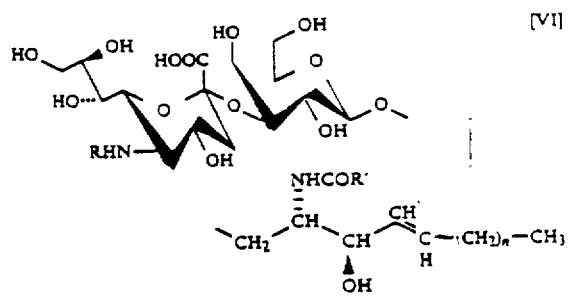

"

and substitute therefor --

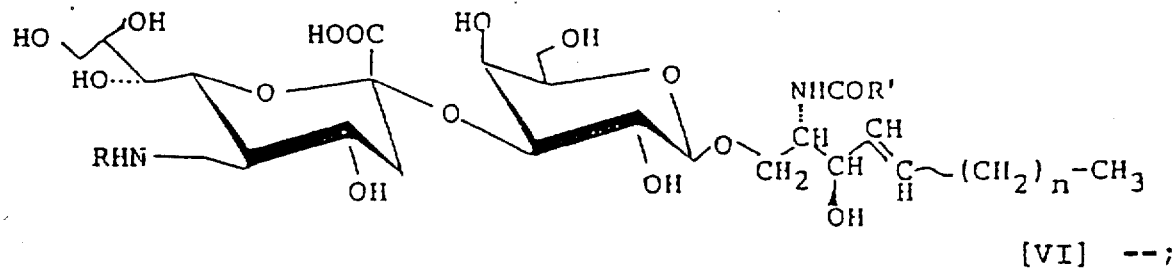

[VI] --;

Formula (III), delete "

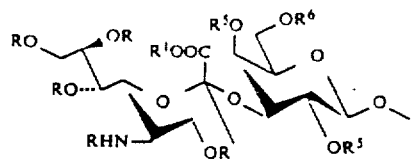

"

UNITED STATES PATENT AND TRADEMARK OFFICE
CERTIFICATE OF CORRECTION

PATENT NO. : 4,918,170
DATED : April 17, 1990
INVENTOR(S) : Akira HASEGAWA et al.

It is certified that error appears in the above-identified patent and that said Letters Patent is hereby corrected as shown below:

"and substitute therefor --

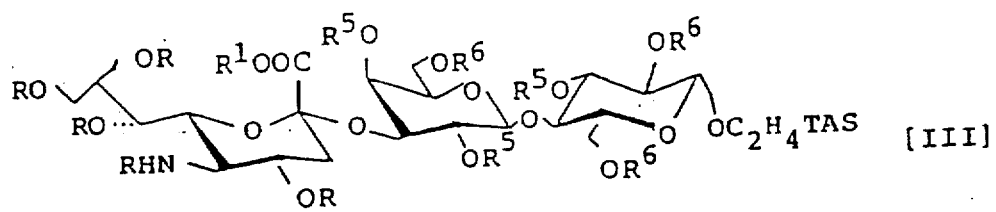

[III]

Column 3, Formula (VIII), delete "

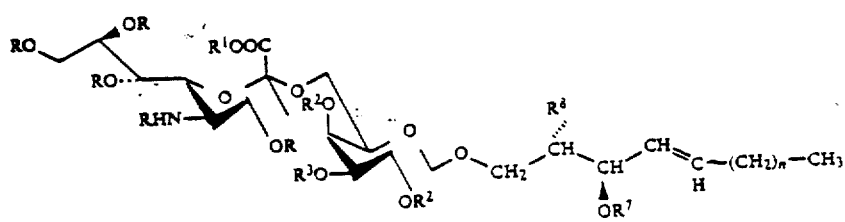

[VIII]

"

and substitute therefor --

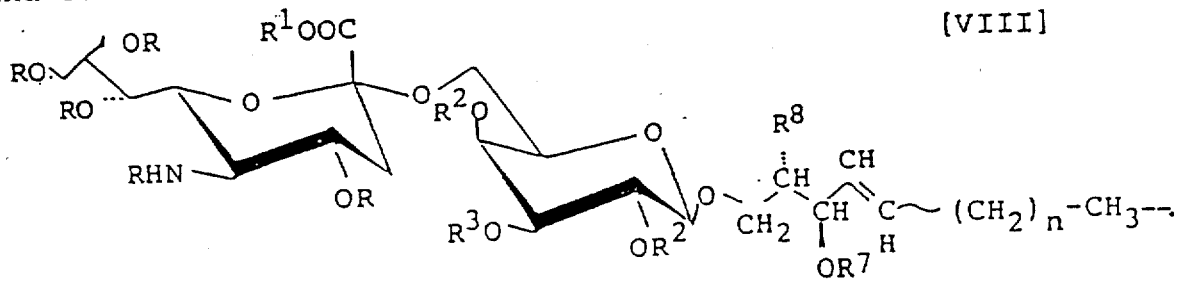

[VIII]

UNITED STATES PATENT AND TRADEMARK OFFICE
CERTIFICATE OF CORRECTION

PATENT NO. : 4,918,170

DATED : April 17, 1990

INVENTOR(S) : Akira HASEGAWA et al.

It is certified that error appears in the above-identified patent and that said Letters Patent is hereby corrected as shown below:

Column 8, Formula (IVa), delete "

and substitute therefor --

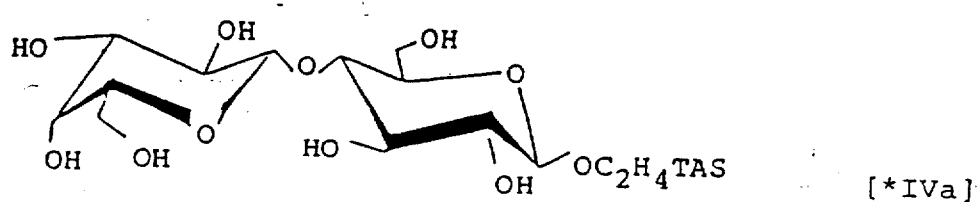

Column 29, Formula (VI), delete "

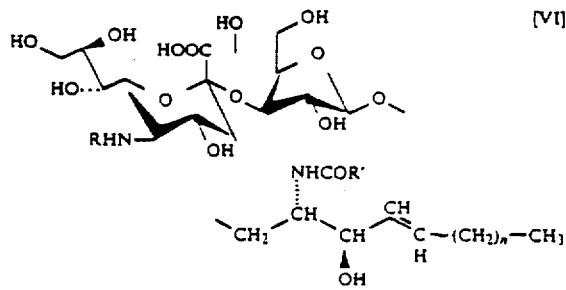

"

UNITED STATES PATENT AND TRADEMARK OFFICE
CERTIFICATE OF CORRECTION

PATENT NO. : 4,918,170
DATED : April 17, 1990
INVENTOR(S) : Akira HASEGAWA et al.

It is certified that error appears in the above-identified patent and that said Letters Patent is hereby corrected as shown below:

and substitute therefor --

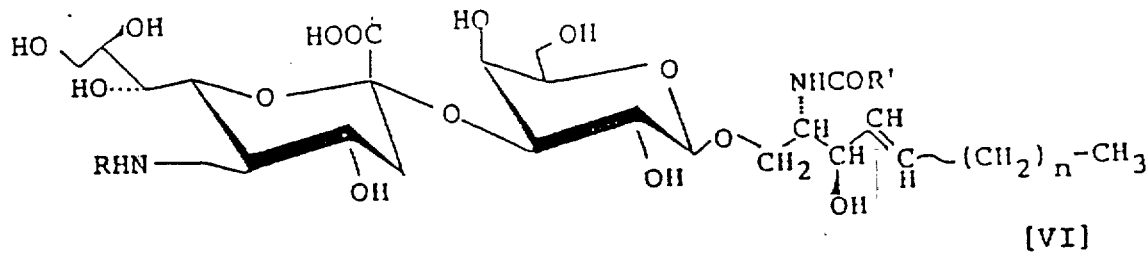

Column 30, Formula (VIII), delete "

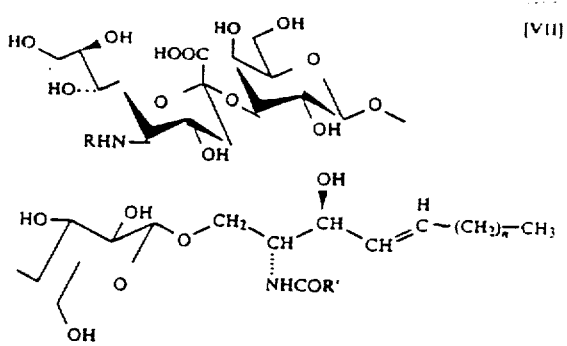

"

and substitute therefor --

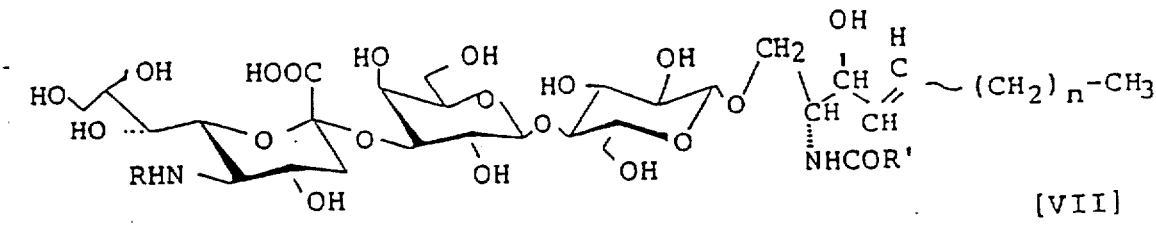

--

UNITED STATES PATENT AND TRADEMARK OFFICE
CERTIFICATE OF CORRECTION

PATENT NO. : 4,918,170
DATED : April 17, 1990
INVENTOR(S) : Akira HASEGAWA et al.

It is certified that error appears in the above-identified patent and that said Letters Patent is hereby corrected as shown below:

Column 30, Formula (I), delete "

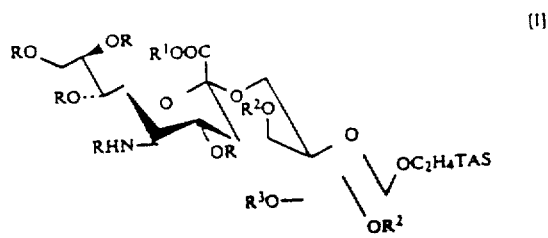

and substitute therefor --

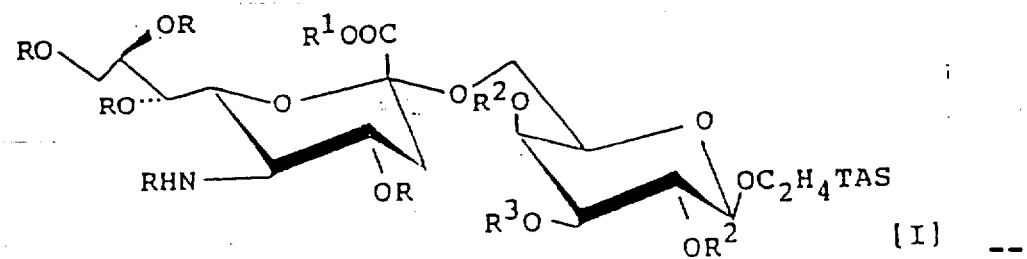

Column 30, Formula (II), delete "

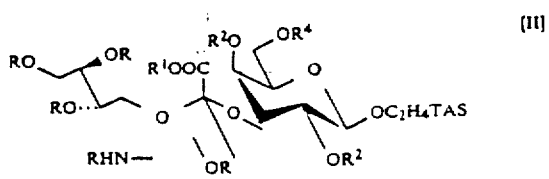

"

UNITED STATES PATENT AND TRADEMARK OFFICE
CERTIFICATE OF CORRECTION

PATENT NO. : 4,918,170

DATED : April 17, 1990

INVENTOR(S) : Akira HASEGAWA et al.

Page 6 of 6

It is certified that error appears in the above-identified patent and that said Letters Patent is hereby corrected as shown below:

and substitute therefor --

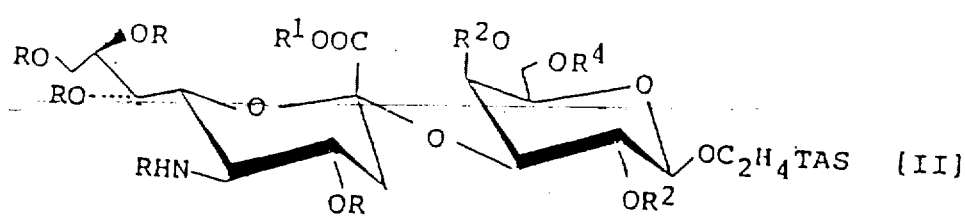

--.

Signed and Sealed this

Nineteenth Day of May, 1992

Attest:

DOUGLAS B. COMER

Attesting Officer

Acting Commissioner of Patents and Trademarks